United States Patent [19]
Gesellchen et al.

[11] Patent Number: 5,430,023
[45] Date of Patent: Jul. 4, 1995

[54] TRIPEPTIDE ANTITHROMBOTIC AGENTS

[75] Inventors: Paul D. Gesellchen, Indianapolis; Robert T. Shuman, Greenwood, both of Ind.

[73] Assignee: Eli Lilly and Company, Indianapolis, Ind.

[21] Appl. No.: 121,134

[22] Filed: Sep. 14, 1993

Related U.S. Application Data

[63] Continuation-in-part of Ser. No. 756,091, Sep. 6, 1991, which is a continuation-in-part of Ser. No. 589,553, Sep. 28, 1990, abandoned.

[51] Int. Cl.$^6$ ............... A61K 38/00; C07K 5/08
[52] U.S. Cl. ............... 514/18; 530/331
[58] Field of Search ............... 514/18; 530/331

[56] References Cited

U.S. PATENT DOCUMENTS

| | | | |
|---|---|---|---|
| 4,316,889 | 2/1982 | Bajusz et al. | 514/18 |
| 4,346,078 | 8/1982 | Bajusz et al. | 514/18 |
| 4,399,065 | 8/1983 | Bajusz et al. | 514/18 |
| 4,478,745 | 10/1984 | Bajusz et al. | 514/18 |
| 4,703,036 | 10/1987 | Bajusz et al. | 514/18 |
| 5,202,416 | 4/1993 | Stueber et al. | 530/322 |

OTHER PUBLICATIONS

Clinical Laboratory Methods and Diagnosis, ed. A. C. Sonnenwirth and L. Jarett, v.1, Chapters 42 and 45, pp. 1020–1025 and 1056 (1980).
Merck Manual of Diagnosis and Therapy, 15th Ed (1987), Merck, Sharp & Dohme Laboratories, Ch 99, pp. 1145–1154.
Zoology, Elliot, A. M., The Meredith Corporation (1968) pp. 725–734.
Goodman and Gilman, The Pharmacological Basis of Therapeutics, Eighth Edition, pp. 1311–1313 (1990).
Sigma Co. Catalog, p. 154 (1992).
Exert, Peptide and Protein Drug Delivery, Vincint Lee, ed. Marcel Dekker, Inc., pp. 288–290 (1991).
Dayhoff, Atlas of Protein Sequence and Structure, 1972, pp. 85–99.
Bagusz, S., et al., J. Med. Chem., 1990, 33, 1729–1735.
Fareed, J., et al., Annals N.Y. Academy of Sciences, 1981, 765–784.
Shuman, et al., Proceedings of the Twelfth American Peptide Symposium, Jun. 16–21, 1991.
Wilson, et al., American Heart Association, Nov. 11–14, 1991, Anaheim Convention Center, Anaheim, Calif.
Bajusz, et al., Int. J. Peptide Res., 12, 1978, 217–221.
Gesellchen, et al., Tenth American Peptide Symposium, May 23–28, 1987, St. Louis, Mo.
Claeson, et al., Proceedings of the Twelfth American Peptide Symposium, Jun. 16–21, 1991, Cambridge, Mass.

(List continued on next page.)

*Primary Examiner*—Jill Warden
*Assistant Examiner*—P. Lynn Touzeau
*Attorney, Agent, or Firm*—John C. Demeter; David E. Boone; Gerald V. Dahling

[57] ABSTRACT

Thrombin inhibitors represented by the formula

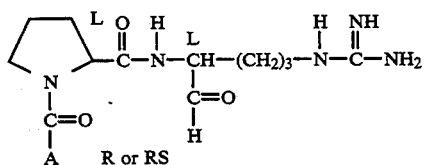

as provided wherein A(C=O)— is, inter alia, phenylglycyl, cyclohexylglycyl, cyclohexenylglycyl, thienylglycyl or naphthylglycyl, wherein the α-amino group is preferably substituted by alkyl e.g. methyl or an alkoxycarbonyl, cycloalkoxycarbonyl or arylkoxycarbonyl group e.g. t-butyloxycarbonyl. A(C=O)— also represents an α-substituted acetyl group such as α-methoxyphenylacetyl; or a bicyclic group such as a tetrahydroisoquinolin-1- or 3-carbonyl group; a perhydroisoquinolin -1- or -3-carbonyl group; or a 1-amino or (substituted amino) cycloalkylcarbonyl group such as 1-aminocyclohexylcarbonyl. Also provided are a method for inhibiting the formation of blood clots in man and animals by administering a thrombin inhibitor of the above formula and pharmaceutical formulations useful in the method.

60 Claims, No Drawings

OTHER PUBLICATIONS

Smith, G. F., Shuman, R. T. Gesellchen, P. D., Craft, T. J., Gifford, P., Kurz, K. D., Jackson, C. V. Sandusky, G. E., and P. D. Williams. A New Family of Thrombin Inhibitors with Improvided Specificity and Therapeutic Index. (Submitted to the American Heart Association, Oct., 1991, Circulation Oct., 1991, vol. 84, II-579, 1991).

Jackson, V., Wilson, H., Frank, J., Crowe, V., Craft, T., and G. Smith. The Thrombin Inhibitor, Methyl-D-Phe-Pro-Arginal—An Effective Adjunct to Coronary Artery Thrombolysis in the Anesthetized Dog. FASEB J. 5(4)A521 (1991).

Crowe, V., Frank, J., Wilson, H., Coffman, B., Smith, G., and V. Jackson. Anticoagulant and Antithrombotic Efficacy of the Thrombin Inhibitor Methyl-D-Phe-Pro-Arginal in a Canine Model of Coronary Thrombosis. FASEB J. 5(4)A521 (1991).

Wilson, H., Frank, J., Crowe, V., Coffman, B., Smith, G., Shuman, R., and V. Jackson. Anticoagulant and Antithrombotic Efficacy of the Novel Thrombin Inhibitor, Methyl-D-Phe-Pro-Arginal, in a Canine Model of Coronary Thrombosis (Arteriosclerosis and Thrombosis, Oct., 1991).

Jackson, V., Wilson, H., Frank, J., Crowe, V., Coffman, B., Shuman, R., and G. Smith. The Novel Thrombin Inhibitor Methyl-D-Phg-Pro-Arginal: An Effective Conjunctive Agent to Coronary Artery Thropmobolysis in the Anesthetized Dog. (Arteriosclerosis and Thrombosis, Oct., 1991).

Shuman, R. T., Rothenberger, R. B., Campbell, C. S. Smith, G. F., Jackson, C. V., Kurz, K. D., and P. D. Gesellchen. Prevention of Reocclusion by a Thrombin Inhibitor. (American Peptide Symposium, Jun., 1991).

Shuman, R. T., Rothenberger, R. B., Campbell, C. S., Smith, G. F., Jackson, C. V., Kurz, K. D., and P. D. Gesellchen. A Series of Highly Active Serine Proteinase Inhibitors. (American Peptide Symposium, Jun., 1991).

Jackson, C. V., Frank, J. D., Crowe, V. G., Craft, T. J., and G. F. Smith. Assessment of the Anticoagulant and Antithrombotic Efficacy of the Thrombin Inhibitor, BOC-Phe-Pro-Arginal, in a Canine Model of Coronary Thrombosis. *Arteriosclerosis,* 10 922A (1990).

Jackson, C. V., Frank, J. D., Crowe, V. G., Craft, T. J., and G. F. Smith. The Thrombin Inhibitor, BOC-Phe-Pro-Arginal. An Effective Adjunct to Coronary Artery Thrombolysis in the Anesthetized Dog. *Arteriosclerosis,* 10 923a (1990).

Shackelford, K. A., Tanzer, R. L., Shuman, R., Gesellchen, P:.D., Grindey, G. B., Sundboom, J. L. Smith, G. F., and R. L. Merriman. Inhibition of Spantaneous Metastasis by Boc-D-Phe-Pro-Arginal. American Association for Cancer Research, San Francisco, 1989. *Proc. Am. Assn. Cancer Res.,* 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund Wistar (LW) Rats to Anti-fibrin Agents. American Association for Cancer Research. New Orleans, May 1988, *Proc. Am. Assn. Cancer Res.,* 29 240 (1988).

Neubauer, B. L., Best, K. L., Gesellchen, P. D., Goode, R. L., Merriman, R. L., Tanzer, L. R., Shaar, C. J., Shuman, R., Sundboom, J. L. and G. F. Smith. Inhibitory Effects of Heparin and BOC-D-Phe-Pro-Arginal on the Metastasis of the PAIII Prostatic Adenocarcinoma in Male Lobund Wistar (LW) Rats. American Urological Association. Boston, May 1988, *J. Urol.,* 139 175A (1988).

Gesellchen, P.-D., Smith, G. F., et al., Anticoagulant, Antithrombotic, and Antimetastatic Effects of a Serine Proteinase Inhibitor. 10th American Peptide Symposium, Washington University, St. Louis, Mo. (1987).

Smith, G. F., Sundboom, J. L., Best, K., Gesellchen, P. D., Merriman, R. L., Shuman, R., and Neubauer, B. L. Heparin, Boc-D-Phe-Pro-Arginal, and Warfarin (Fibrin Antagonists) Inhibit Metastasis in an In Vivo Model. American Chemical Society National Meeting. Abstract BIOL 70 Biochemistry (1987).

K. D. Kurz, T. Smith, R. A. Moore, and B. W. Main. Comparison of Thrombin Inhibitors in Rat Models of Thrombosis and Thrombolysis. FASEB Journal, vol. 5 (No. 4), 1991.

Tomori et al., Chromatographia, vol. 19, 437–442 (1984).

European Search Report for EP 91308785.4.

J. of Medicinal Chemistry—1993.

Eur. Pat. 48982—not provided.

TRIPEPTIDE ANTITHROMBOTIC AGENTS

CROSS REFERENCE TO RELATED APPLICATIONS

This application is a continuation-in-part of application Ser. No. 07/756,091 filed Sep. 6, 1991, which application is a continuation-in-part of application Ser. No. 07/589,553 filed Sep. 28, 1990, now abandoned.

BACKGROUND OF THE INVENTION

This invention relates to thrombin inhibitors which are useful anticoagulants in humans and animals. In particular it relates to derivatives of the dipeptide L-Proline-L-Arginine aldehyde having high antithrombotic activity.

Thrombin inhibition is currently achieved by the administration of heparins and coumarins. The mechanism by which these agents act has been much studied. Heparins are only administerable parenterally and levels must be carefully monitored. Coumarins act by blocking or inhibiting the formation of prothrombin and require some time to achieve maximum effectiveness.

Although both the heparins and the coumarins are effective anticoagulants there exists a need for antithrombin agents which act quickly to prevent clot formation and which do not interfere with plasmin action in dissolving existing clots.

SUMMARY OF THE INVENTION

The thrombin inhibiting compounds provided by this invention are represented by the following formula 1.

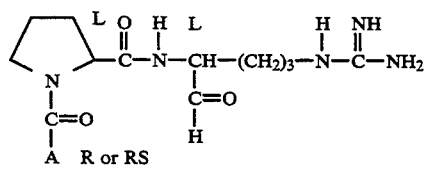

wherein A is
1) a group of the formula

wherein R is a phenyl group of the formula

wherein a and a' independently are hydrogen, lower alkyl, lower alkoxy, halogen, trifluoromethyl, hydroxy, hydroxymethyl, amino, or aminomethyl; or R is thienyl, furyl, naphthyl, or naphthyl mono- or disubstituted by lower alkyl, lower alkoxy, halogen, amino, or mono- or di-(lower alkyl)amino, or hydroxy; or R is cyclohexadienyl, cyclohexenyl, cyclohexyl or cyclopentyl;
$R_1$ is hydrogen, methyl or ethyl;
B is lower alkyl, lower alkoxy, hydroxy, or an amino group of the formula

—N($R_2$)($R_3$)

wherein $R_2$ and $R_3$ independently are hydrogen or lower alkyl, or $R_2$ is hydrogen and $R_3$ is acetyl, haloacetyl or an oxycarbonyl group of the formula $R_4$—OC(O)— wherein $R_4$ is $C_1$–$C_6$ alkyl, $C_2$–$C_6$ alkenyl, $C_3$–$C_7$ cycloalkyl, benzyl, nitrobenzyl, diphenylmethyl, or a phenyl group as defined above; provided further that when $R_1$ is methyl or ethyl then B is other than methyl or ethyl or A is
2) 1-aminocyclohexyl or 1-aminocyclopentyl wherein the amino group is an —N($R_2$)($R_3$) group as defined above; or A is
3) a bicyclic group of the formula 2

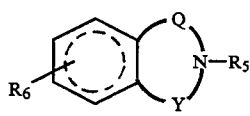

wherein Q is a one carbon radical represented by

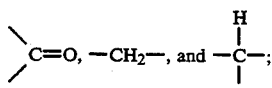

or a two carbon radical represented by

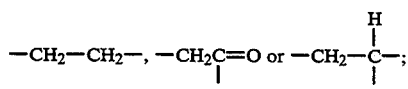

Y is a one carbon radical represented by

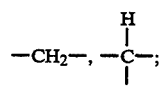

or a two carbon radical represented by

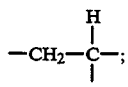

provided that one, but not both, of Q and Y is

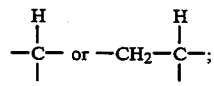

and, provided further that, only one of Q and Y is a two carbon radical;
$R_5$ is hydrogen or an oxycarbonyl group as defined above; and $R_6$ is hydrogen, halogen, hydroxy, lower alkyl or lower alkoxy; and the dotted circle within the 6-membered ring of the bicyclic group indicates an aromatic ring or a perhydro ring;

and the pharmaceutically acceptable non-toxic salts thereof.

The peptides represented by the formula 1 are useful antithrombotic agents and can be used as adjuncts to tissue plasminogen activator (tPA), streptokinase or urokinase therapy.

The compounds are prepared by conventional coupling methods. For example, Boc-D-Phg is coupled with an ester of L-proline to form Boc-D-Phg-Pro ester. The ester group is removed and the Boc-D-Phg-Pro is coupled with the lactam form of L-arginine to provide Boc-D-Phg-Pro-Arg lactam in amino protected form. The Arg lactam ring is opened by reduction and the arginine amino protecting group removed to provide Boc-D-Phg-Pro-Arg aldehyde. The peptides are converted to suitable salt forms such as the acetates and sulfates.

The invention also provides a method for preventing the formation of clots in man and animals and pharmaceutical formulations useful in the method.

DETAILED DESCRIPTION

The compounds of the invention represented by the formula 1 are tripeptides when A is an amino acid residue such as phenylglycyl (Phg), and when A is other than an amino acid residue, e.g. when B is a group other than an amino or alkylamino group, the compounds are N-acyl derivatives of the dipeptide proline and arginine aldehyde (Pro-Arg-H). As shown in formula 1, the asymmetric center of the A(C=O) moiety is R or RS while that of the proline and arginine aldehyde moieties is L.

The terms used in formula 1 are defined herein as follows:

Lower alkyl refers to the straight and branched chain $C_1$–$C_4$ alkyl groups such as methyl, ethyl, n-propyl, isopropyl, n-butyl and the like.

Lower alkoxy refers to $C_1$–$C_4$ alkoxy group such as methoxy, ethoxy, n-propoxy, isopropoxy, n-butoxy, t-butoxy and the like.

Halogen refers to fluoro, chloro, bromo or iodo.

Mono- or di-(lower alkyl)amino refers to such groups as methylamino, ethylamino, dimethylamino, methylethylamino, diethylamino, n-butylamino, n-propylamino and the like.

The term "$C_1$–$C_6$ alkyl" refers to the straight and branched alkyl groups such as the $C_1$–$C_4$ alkyl groups defined above and, in addition, n-pentyl, isopentyl, n-hexyl, the isomeric hexyl groups, and the like. "$C_2$–$C_6$ alkenyl" refers to the olefinic groups such as vinyl, allyl, butenyl, isomeric pentenyl and hexenyl groups. "$C_3$–$C_7$ Cycloalkyl" refers to the cyclic hydrocarbons having from three to 7 ring carbon atoms such as cyclopropyl, cyclobutyl, cyclopentyl, cyclohexyl and cycloheptyl.

As defined in formula 1, when A is the group $(R)(R_1)(B)C$—, R can be a phenyl group which may be mono- or di-substituted. Examples of such phenyl groups are phenyl (a and a'=H), 4-methylphenyl, 3-ethylphenyl, 4-methoxyphenyl, 3-methoxyphenyl, 3-ethoxyphenyl, 2-methoxyphenyl, 3-isopropoxyphenyl, 4-hydroxyphenyl, 4-chlorophenyl, 3-chlorophenyl, 2-fluorophenyl, 3-fluorophenyl, 3-bromophenyl, 4-fluorophenyl, 3-trifluoromethylphenyl, 4-trifluoromethylphenyl, 4-hydroxymethylphenyl, 2-hydroxymethylphenyl, 3-aminophenyl, 4-aminophenyl, 3-amino-4-chlorophenyl, 3,4-dichlorophenyl, 3-hydroxy-4-fluorophenyl, 3-hydroxy-4-methylphenyl, 3-methoxy-4-hydroxyphenyl, 3-chloro-4-ethoxyphenyl, and like mono- or di-substituted phenyl groups.

Examples of R groups when R is naphthyl or a mono- or di-substituted naphthyl group are 1-naphthyl, 2-naphthyl, 6-methoxy-2-naphthyl, 8-hydroxy-1-naphthyl, 8-amino-2-naphthyl, 4-methyl-1-naphthyl, 6-chloro-2-naphthyl, 4-hydroxy-6-ethoxy-2-naphthyl, 8-methylamino-4-chloro-2-naphthyl, 6,8-dimethoxy-2-naphthyl, 6-ethyl-1-naphthyl, 4-hydroxy-1-naphthyl, 3-methoxy-1-naphthyl, and like naphthyl groups.

Examples of groups represented in the formula 1 when B is an amino group —$N(R_2)(R_3)$ are amino ($R_2=R_3=H$), methylamino, ethylamino, isopropylamino, dimethylamino, and like amino groups; and when $R_2$ is hydrogen and $R_3$ is an oxycarbonyl group $R_4$—O—C(O)—, examples of such groups, are the $C_1$–$C_6$ alkoxycarbonylamino groups such as methoxycarbonylamino, ethoxycarbonylamino, t-butoxycarbonylamino, isoamyloxycarbonylamino and the like; the $C_2$–$C_6$ alkenyloxycarbonylamino groups such as vinyloxycarbonylamino, allyloxycarbonylamino, 2-butenyloxycarbonylamino, and the like; $C_3$–$C_7$ cycloalkoxycarbonylamino groups such as cyclopropyloxycarbonylamino, cyclopentyloxycarbonylamino, cyclohexyloxycarbonylamino, and the like. Oxycarboxylamino groups represented by the term B further include for example, benzyloxycarbonylamino, 4-nitrobenzyloxycarbonylamino, diphenylmethoxycarbonylamino, phenyloxycarbonylamino, or a substituted phenyloxycarbonylamino group wherein the substituted phenyl moiety is as defined hereinabove, and the like.

Examples of the groups A(C=O) of the formula 1 when A is a group 1 radical of the formula $(R)(R_1)(B)C$— are phenylglycyl, 3-methoxyphenylglycyl, 4-methoxyphenylglycyl, 4-chlorophenylglycyl, 3,4-dichlorophenylglycyl, 3-trifluoromethylphenylglycyl, N-(t-butyloxycarbonyl)phenylglycyl, N-(t-butyloxycarbonyl-N-methyl)phenylglycyl, α-methylphenylacetyl, α-ethylphenylacetyl, α-methoxyphenylacetyl, α-isopropoxyphenylacetyl, 1-naphthylglycyl, 2-naphthylglycyl, N-(t-butyloxycarbonyl)-2-naphthylglycyl, 2-thienylglycyl, 3-thienylglycyl, N-(cyclopentyloxycarbonyl)-2-thienylglycyl, 2-furylglycyl, N-ethyl-2-furylglycyl, mandeloyl, 4-chloromandeloyl, 3-methoxymandeloyl, α-hydroxy-α-(2-naphthyl)acetyl, α-hydroxy-α-(2-thienyl)acetyl, 1,4-cyclohexadienylglycyl, 1-cyclohexenylglycyl, N-(t-butyloxycarbonyl)-1,4-cyclohexadienylglycyl, cyclohexyglycyl, and like A(CO) groups.

The peptide compounds represented by the formula 1 wherein A is an achiral 1-aminocyclopentyl or 1-amino cyclohexyl group are depicted by the following structural formula.

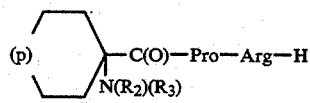

wherein p is a carbon to carbon bond or —$CH_2$—; and $R_2$ and $R_3$ have the same meanings as defined hereinabove. Examples of such tripeptides are N-(1-aminocyclohexanoyl)-Pro-Arg-H, N-(1-aminocyclopentanoyl)-Pro-Arg-H; N-(1-methylaminocyclohexanoyl)-Pro-Arg-H, N-(1-t-butyloxycarbonylaminocyclohexanoyl)-Pro-Arg-H, and the like.

Examples of peptides represented by the formula 1 wherein A is a bicyclic group represented by the foregoing formula 2 are the D-1,2,3,4-tetrahydroisoquinolin-1-carbonyl and D-1,2,3,4-tetrahydroisoquinolin-3-carbonyl N-acyl derivatives of Pro-Arg-H depicted below,

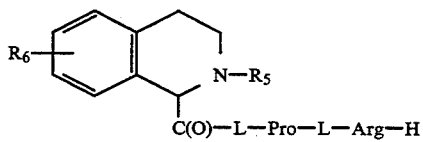

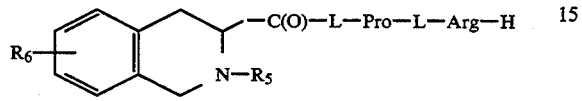

the dihydroisoindole-1-carbonyl derivatives depicted below;

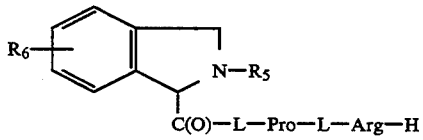

the oxo derivatives represented by the formulas

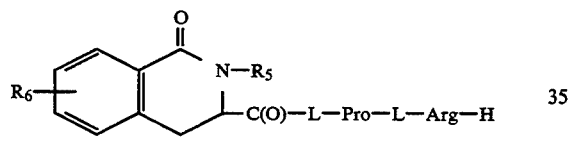

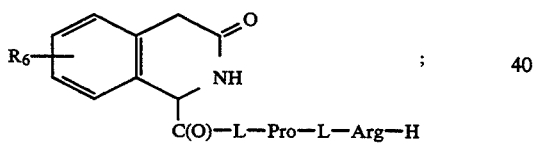

;

and the perhydroderivatives including D-1,2,3,4,4a,5,6,7,8,8a-decahydroisoquinolin-1-carbonyl (perhydroisoquinolin-1-carbonyl or 1-Piq) and D-1,2,3,4,4a,5,6,7,8,8a-decahydroisoquinolin-3-carbonyl perhydroisoquinolin-3-carbonyl or 3-Piq) derivatives of Pro-Arg-H depicted below.

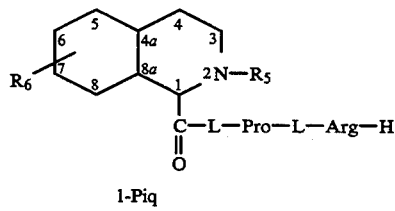

1-Piq

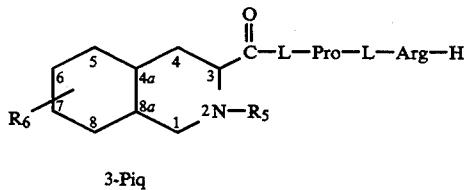

3-Piq

The terms $R_6$ and $R_5$ have the same meanings as defined hereinabove. $R_5$ is preferably hydrogen, and $R_6$ is preferably hydrogen, methoxy, ethoxy, chloro, or methyl.

The perhydro derivatives can exist as cis or trans stereoisomers. For example, the following pair of stereoisomers identified as cis can be formed for D-perhydroisoquinolin-1-carbonyl-L-prolyl-L-arginine aldehyde:

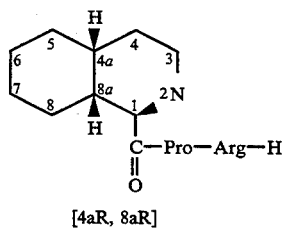

[4aR, 8aR]

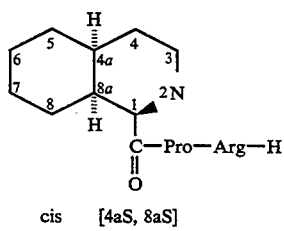

cis    [4aS, 8aS]

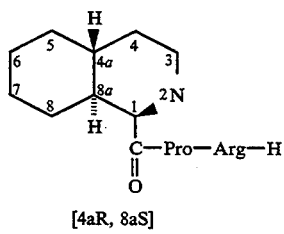

[4aR, 8aS]

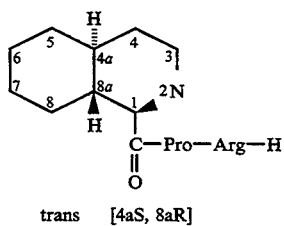

trans    [4aS, 8aR]

Pharmaceutically acceptable salts of peptides of the invention include the acid addition salts formed with inorganic acids and carboxylic acids. Examples of inorganic acids forming salts are the hydrohalic acids hydrochloric and hydrobromic; phosphoric acid and sulfuric acid. Carboxylic acid salts are formed with acids such as acetic, propionic, malonic, maleic, citric, succinic, malic, benzoic, fumaric, and like carboxylic acids. The acid addition salts are prepared in a conventional manner e.g. by neutralizing the free base form of the compound 1 with the acid. Preferred acid addition salts are sulfate and hydrochloride salts.

Preferred embodiments of the invention are compounds represented by the formula 1 wherein A is

where R is a phenyl group

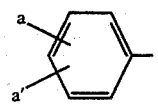

or a naphthyl or substituted naphthyl group, $R_1$ is hydrogen and B is an amino group $-N(R_2)(R_3)$. Further preferred compounds are represented when $R_2$ is hydrogen and $R_3$ is an oxycarbonyl group $R_4O-C(O)-$.

A further preferred embodiment of the invention comprises compounds of the formula 1 wherein A is a bicyclic group (2). Preferred compounds of this embodiment are represented by the formula 1 when $A(C=O)$ is 1,2,3,4-tetrahydroisoquinolin-1-carbonyl or perhydroisoquinolin-1-carbonyl (formula 2, $Q=-CH_2-CH_2-$,

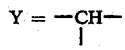

and, $R_5=R_6=H$) and 1,2,3,4-tetrahydroisoquinolin-3-carbonyl or perhydroisoquinolin-3-carbonyl (formula 2,

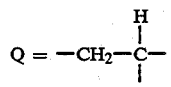

and $Y=-CH_2-$).

The compounds represented by the formula 1 are prepared by known methods of peptide coupling. According to one such method the acid A-COOH, wherein A has the same meanings as defined for formula 1, is coupled with a carboxy protected proline to form the dipeptide (when A is an amino acid) or an N-acylproline ester (when A is other than an amino acid). The carboxy protecting ester group of the proline moiety of the product is removed and the free acid form of the dipeptide is coupled with the lactam form of arginine. The above reaction sequence is illustrated by the following scheme.

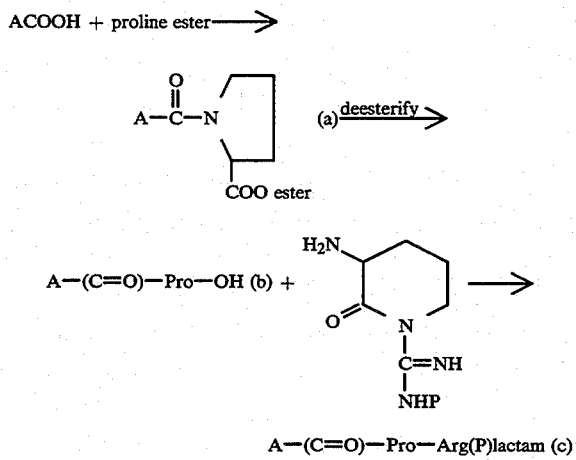

wherein P represents an amino protecting group.

The coupled Arg(P) lactam product (c) is reduced with lithium aluminum hydride in an inert solvent to cleave the lactam ring and provide the tripeptide in the arginine aldehyde form represented by the formula A(C=O)-Pro-Arg(P)-H wherein Arg(P)-H represents amino protected arginine aldehyde.

The lactam form of arginine is obtained by intramolecular coupling of amino protected arginine [Arg-OH]. For example, Boc-Arg(Cbz)OH represented by the formula

is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of a stronger tertiary amine base such as triethylamine effects the internal acylation to provide the lactam form of the di-amino protected arginine as shown below.

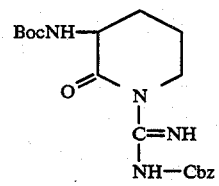

Prior to use in the coupling with the A(C=O)-Pro-OH as shown in the above scheme, the Boc protecting group is selectively removed with trifluoroacetic acid to provide the requisite free amino group.

The coupling of an ACOOH compound with a proline ester, when A is an amino acid residue, is carried out by first protecting the amino group of the amino acid. Conventional amino protecting groups commonly used for temporary protection or blocking of the amino group are employed. Examples of such protecting groups include the alkoxy, alkenyloxy, cycloalkoxy and aryloxycarbonyl groups such as ethoxycarbonyl, t-butyloxycarbonyl (Boc), cyclohexyloxycarbonyl, adamantyloxycarbonyl, trichloroethoxycarbonyl, benzyloxycarbonyl (Cbz), diphenylmethoxycarbonyl, and like groups. The ester group employed to protect the carboxy group of proline during the coupling reaction can be any of the commonly used readily removable ester groups such as t-butyl, benzyl, p-nitrobenzyl, p-methoxybenzyl, diphenylmethyl, trichloroethyl, phenacyl, or trialkylsilyl esters. In carrying out the coupling reaction one employs an ester group for proline which is removable by conditions under which the amino protecting group remains intact. The amino protecting group of the acylating acid ACOOH thus remains in place for protection of the amino group during the subsequent coupling with the arginine lactam compound to form c.

The compounds represented by the formula 1 wherein A is the group $(R)(R_1)(B)C-$ and B is an amino group $-N(R_2)(R_3)$ wherein $R_2$ is hydrogen and $R_3$ is lower alkyl are prepared with the corresponding compound wherein B is amino by using known alkylation methods. For example, N-methyl-D-phenylglycyl- L-prolyl-L-arginine aldehyde is prepared by reductive alkylation as follows. Cbz protected D-phenylglycine is coupled in DMF with L-proline t-butyl ester using dicyclohexylcarbodiimide (DCC) and hydroxybenzotriazole (HOBt) to form the dipeptide Cbz-D-phenylglycyl-L-proline t-butyl ester. The peptide is hydrogenated in ethyl alcohol over palladium on carbon catalyst to remove the Cbz protecting group, formaldehyde is added to the reduction mixture and the hydrogenation is continued to form N-methyl-D-phenylglycyl-L-proline t-butyl ester. The N-methyl secondary amino group of the phenylglycyl moiety is protected with the Cbz group by reacting the dipeptide t-butyl ester with benzyl chloroformate in THF containing N-methylmorpholine to form N-Cbz-N-methyl-D-phenylglycyl-L-proline t-butyl ester. The t-butyl ester group is removed at room temperature in trifluoroacetic acid containing anisole to provide N-Cbz-N-methyl-D-phenylglycyl-L-proline. The latter dipeptide is then coupled to the Cbz protected Arg lactam and the lactam ring reductively opened to the Arg aldehyde as described above. Both of the Cbz protecting groups of the tripeptide are removed by hydrogenation over Pd/C catalyst to provide N-methyl-D-phenylglycyl-L-prolyl-L-arginine aldehyde.

Compounds represented by the formula 1 wherein A is $(R)(R_1)(B)C-$, and R is cyclohexadienyl or cyclohexenyl and B is an alkylamino group, $-N(R_2)(R_3)$ can be prepared by reduction of the imine formed with a lower alkyl aldehyde with sodium cyanoborohydride. Likewise such N-alkylations can be carried out with a lower alkyl iodide and sodium hydride.

The compounds of the formula 1 wherein A is a bicyclo group (2) are prepared by the same coupling methods as above. For example the peptide of formula 1 wherein A represents the 1,2,3,4-tetrahydroisoquinolin-1 group is obtained by acylation of an ester of proline, such as the benzyl ester, with an active derivative of 1,2,3,4-tetrahydro-1-carboxyisoquinoline. Active derivatives that can be used include the acid halides such as the chloride or bromide, the acid azide, as well as active esters and anhydrides such as those formed with the chloroformates as described above. The ring nitrogen of the tetrahydroisoquinoline (formula 2, $R_5=H$) is protected or alkylated during the acylative coupling. For example an active ester of N-Boc-1,2,3-4-tetrahydro-1-carboxy-isoquinoline formed with iso-butyl chloroformate is used in the acylation of the proline ester. The peptide product N-Boc-1,2,3,4-tetrahydroisoquinolin-1-carbonyl-proline ester is deesterified, the free acid converted to an active ester and the latter coupled to the lactam form of arginine. The lactam product is then converted to the aldehyde form as described above to provide the compound of the formula 1 namely, Boc-1,2,3,4-tetrahydroisoquinolin-1-carbonyl-Pro-Arg-H.

The perhydro bicyclo groups represented by the formula 2 are prepared by hydrogenation of either the partially reduced or unsaturated acids by conventional procedures. For example, 1,2,3,4-tetrahydroisoquinoline-1-carboxylic acid is hydrogenated over platinum oxide in a solvent such as ethanol or acetic acid to provide the perhydro(decahydro) isoquinolin-1-carboxylic acid. The perhydro acids are then used as described above in the acylation of a proline ester. Examples of such perhydro derivatives represented by the formula 1 are N-(D-decahydroisoquinolin-1-carbonyl)-L-prolyl-L-arginine aldehyde and N-(D-decahydroisoquinolin-3-carbonyl)-L-prolyl-L-arginine aldehyde.

The above described hydrogenation process provides a mixture of the cis and trans stereoisomers discussed hereinabove with the cis stereoisomers being formed in the greater amount. It is contemplated and intended that all the stereoisomers of all compounds of formula 1 are within the scope of the present invention. For example, preferred compounds include D-1-(4aS, 8aS)-Piq-(L)-Pro-(L)-Arg-H, D-1-(4aR, 8aR)-Piq-(L)-Pro-(L)-Arg-H, D-1-(4aS, 8aR)-Piq-(L)-Pro-(L)-Arg-H, D-1-(4aR, 8aS)-Piq-(L)-Pro-(L)-Arg-H, D-3-(4aS, 8aS)-Piq-(L)-Pro-(L)-Arg-H, D-3 -(4aR, 8aR)-Piq-(L)-Pro-(L)-Arg-H, D-3-(4aS, 8aR)-Piq-(L)-Pro-(L)-Arg-H, and D-3-(4aR, 8aS)-Piq-(L)-Pro-(L)-Arg-H.

The coupling reactions described above are carried out in the cold preferably at a temperature between about $-20°$ C. and about $15°$ C. The coupling reactions are carried out in an inert organic solvent such as dimethylformamide, dimethylacetamide, tetrahydrofuran, methylene chloride, chloroform, and like common solvents. Generally anhydrous conditions are used when, in the coupling reaction, an active ester of the acylating acid is used.

The compounds of the invention are isolated best in the form of acid addition salts. Salts of the compounds of formula 1 formed with acids such as those mentioned hereinabove useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalene sulfonic acid may be so used.

A preferred method for isolating and purifying the compounds represented by the formula 1 while at the same time preparing a desired stable salt form involves preparative purification over $C_{18}$ reversed-phase chromatography. The aqueous phase comprises sulfuric acid or hydrochloric acid at a concentration between about 0.01% and about 0.05% and acetonitrile, THF, methanol or other suitable solvent serves as the organic component. The pH of the acidic eluant is adjusted to between about pH 4 and about pH 6, the exact pH being a function of the particular peptide, with a basic resin e.g. Bio-Rad AG-1X8 resin in the hydroxyl form. After pH adjustment the solution of the tripeptide salt e.g. sulfate or hydrochloride, is lyophilized to provide the purified salt dry powder form. In an example of the process crude D-Phg-L-Pro-L-Arg-H sulfate, contaminated with the epimeric D-Arg-H sulfate is dissolved in ca 0.01% sulfuric acid and the solution is loaded on a Vydac $C_{18}$ RP-HPLC column. A gradient of 2–10% acetonitrile in 0.01% $H_2SO_4$ was used to elute the column over 10 hours. Multiple fractions are collected and those containing the desired product as determined by analytical RP-HPLC are pooled. The pH of the pooled fractions is adjusted to about pH 4.0 to about pH 4.5 with the Bio-Rad AG-1X8 resin in the hydroxyl cycle. After filtering the solution is lyophilized to provide pure D-Phg-L-Pro-L-Arg-H sulfate.

The compounds provided by the invention (formula 1) inhibit the action of thrombin in man and animals. The inhibition of thrombin is demonstrated by in vitro inhibition of amidase activity of thrombin. The following Table 1 lists the apparent equilibrium constant (Kass) for interaction between the test compound (inhibitor) and thrombin. The data in the table were obtained in an assay in which thrombin hydrolyzes the chromogenic substrate, N-benzoyl-D-phenylalanyl-L-valyl-L-arginyl-p-nitroanilide.

The assay was carried out in 50 μl buffer (0.03M Tris, 0.15M NaCl, pH 7.4) with 25 μl of bovine thrombin solution (0.21 mg/ml of thrombostat powder in 0.06M Tris, 0.3M NaCl, pH 7.4) and 150 μl of an aqueous solution of the chromogenic substrate at a concentration of 0.25 mg/ml. Solutions of test compound (25 μl) at various concentrations were added. Rates of hydrolysis of the substrate were measured by monitoring the reactions at 405 nm for the release of p-nitroaniline. Standard curves were constructed by plotting free thrombin concentration against hydrolysis rate. The hydrolysis rates observed with test compounds are then converted to "free thrombin" values in the respective assays by use of the standard curves. The bound thrombin (bound to test compound) was calculated by subtracting the amount of free thrombin observed in each assay from the known initial amount of thrombin used in the assay. The amount of free inhibitor in each assay was calculated by subtracting the number of moles of bound thrombin from the number of moles of added inhibitor (test compound).

The same procedure was used for human thrombin using test solutions of the thrombin obtained from Inzyme Research Laboratories of South Bend, Ind.

The Kass value is the hypothetical equilibrium constant for the reaction between thrombin and the test compound (I).

$$\text{Thrombin} + I \rightleftharpoons \text{Thrombin} - I$$

$$\text{Kass} = \frac{[\text{Thrombin } I]}{[(\text{Thrombin}) \times (I)]}$$

Kass was calculated for a range of concentrations of compounds and the mean value is reported in units of liter per mole.

TABLE 1

| Inhibition of Thrombin Amidase Activity | |
|---|---|
| Test Inhibitor[1] A(C=O)— (1/mole) | Thrombin Amidase Kass × $10^6$ |
| D-Phenylglycyl | 75 |
| Boc-D-phenylalanyl | 21 |
| Boc-D-phenylglycyl | 88 |
| Boc-D-phenylglycyl | 73 |
| Boc-D-phenylglycyl (sulfate salt) | 107 |
| Boc-D-(4-hydroxy)phenylglycyl | 115 |
| Boc-D-(4-methoxy)phenylglycyl | 75 |
| Boc-DL-(3,4-dichloro)phenylglycyl | 40 |

TABLE 1-continued

| Inhibition of Thrombin Amidase Activity | |
|---|---|
| Test Inhibitor[1] A(C=O)— (1/mole) | Thrombin Amidase Kass × $10^6$ |
| Acetyl-D-(4-methoxy)phenylglycyl | 15 |
| Boc-D-1-naphthylglycyl | 52 |
| Boc-D-2-naphthylglycyl | 22 |
| Boc-DL-1-naphthylglycyl | 18 |
| Boc-D-(6-methoxy)-2-naphthylglycyl | 6 |
| Boc-D-2-thienylglycyl | 14 |
| Boc-D-cyclohexylglycyl | 120 |
| Boc-N-methyl-D-phenylglycyl | 5 |
| (R)-α-Methylphenylacetyl | 11 |
| (R)-α-Ethylphenylacetyl | 7 |
| (R)-α-Methoxyphenylacetyl | 4 |
| (S)-α-Methylphenylacetyl | 0.2 |
| Boc-DL-1,2,3,4-tetrahydroisoquinolin-1-carbonyl | 4 |
| DL-1,2,3,4-Tetrahydroisoquinolin-1-carbonyl | 87 |
| D-1,2,3,4-Tetrahydroisoquinolin-1-carbonyl (sulfate) | 113 |
| D-Perhydroisoquinolin-1-carbonyl | 69 |
| D-1,2,3,4-Tetrahydroisoquinolin-3-carbonyl (sulfate) | 63 |
| Boc-DL-Phg(3-Trifluoromethyl) | 50 |
| Boc-D-Phg(4-Fluoro) | 44 |
| D-Perhydroisoquinolin-3-carbonyl (sulfate) | 25 |
| D-1,2,3,4-Tetrahydroisoquinoiin(1-keto)-3-carbonyl (HCl) | 6 |
| [4aS,8aS]-D-perhydroisoquinolin-1-carbonyl (HCl) | $302^2$ |
| [4aS,8aS]-D-perhydroisoquinolin-3-carbonyl | $56^2$ |
| [4aR,8aR]-D-perhydroisoquinolin-3-carbonyl (sulfate) | $214^2$ |
| $N^\alpha$-Methyl-D-phenylglycyl (sulfate) | 80 |
| $N^\alpha$-Methyl-D-phenylalanyl (sulfate) | 180 |
| $N^\alpha$-ethylcarbamate-1-aminocyclohexane-1-carbonyl | 1.5 |
| $N^\alpha$-acetyl-1-aminocyclohexane-1-carbonyl | 0.2 |

[1]A(C=O)— refers to formula 1. Unless indicated otherwise the test inhibitors were in the form of acetate salts and bovine thrombin was used.
[2]Human thrombin The anticoagulant activity of the compounds of the invention has been determined in standard tests. The following Table 2 presents the data obtained with representative compounds of the invention in tests used to determine prothrombin time, thrombin time and activated partial thromboplastin time (APTT). The numerical values in the table are the concentrations of the test compounds (ng/ml) required to prolong coagulation by 2-fold in the three tests. The thrombin time evaluation was carried out in plasma and separately determined in a buffer system at pH 7.5.

TABLE 2

| Anticoagulant Activity of Thrombin Inhibitors | | | | |
|---|---|---|---|---|
| Test Inhibitor[1] A(C=O) | Plasma Coagulation Assay[2] | | | Buffer (pH 7.5)[2] |
| | Prothrombin Time | APTT[3] | Thrombin Time | Thrombin Time |
| D-Phenylglycyl | 91 | 1139 | 91 | HA[4] |
| N-Boc-D-Phenylglycyl[5] | 667 | 1169 | 110 | 118 |
| N-Boc-D-(4-methoxy)phenylglycyl | NA | 640 | 80 | NA |
| N-Boc-D-(4-hydroxy)phenylglycyl | 1636 | 1091 | 182 | NA |
| N-Boc-DL-1-naphthylglycyl | 1136 | 2272 | 320 | 112 |
| N-Boc-D-1-naphthylglycyl | 1225 | 3100 | 230 | 105 |
| N-Boc-D-2-naphthylglycyl | 1200 | 1200 | 230 | 142 |
| N-Acetyl-D-(4-methoxy)phenylglycyl | 900 | 2600 | 460 | NA |
| N-Boc-D-(6-methoxy)-2-naphthylglycyl | 35489 | 2239 | 460 | 466 |
| N-Boc-D-Cyclohexylglycyl | 522 | 748 | 79 | 60 |
| N-Boc-N-Methyl-D-Phenylglycyl | 300 | 4545 | 300 | NA |
| H-Methyl-D-Phenylglycyl | 899 | >909 | 92 | 67 |
| (R)-α-Ethylphenylacetyl | 700 | 2275 | 115 | NA |

TABLE 2-continued

| Test Inhibitor[1] | Anticoagulant Activity of Thrombin Inhibitors | | | |
|---|---|---|---|---|
| | Plasma Coagulation Assay[2] | | | Buffer (pH 7.5)[2] |
| A(C=O) | Prothrombin Time | APTT[3] | Thrombin Time | Thrombin Time |
| (R)-α-Methoxyphenylacetyl | >909 | >909 | 139 | 173 |

[1]A(C=O) for formula 1
[2]Concentration (ng/ml) of test compounds required to prolong coagulation by 2-fold
[3]APTT = Activated Partial Thromboplastin Time
[4]NA = Not available
[5]The values are averages of 8 assays The data presented in Table 2 were obtained using a CoaScreener instrument from Tecan, Inc. in the assay protocols listed below.

Prothrombin Time:
50 μl plasma
50 μl saline
7 μl test solution
50 μl thromboplastin (Dade)

Thrombin Time:
50 μl plasma
50 μl saline
7 μl test compound
50 μl bovine thrombin (2 NIH unit/ml)

In the Thrombin Time determined in pH 7.4 buffer fibrinogen was used instead of plasma.

APTT:
50 μl plasma
50 μl Actin (Dade)
7 μl test solution
50 μl CaCl$_2$ (0.01 M)

The antithrombotic activity of representative compounds of the invention was determined in in vivo tests carried out in the rat. The test employed induced arterial thrombosis in the carotid artery of the rat and measured the infusion dose of test compound required to maintain blood flow for fifty minutes past the time of occlusion. The test was performed as follows.

Arterial thrombosis was induced in the rat by injury of the carotid artery. Topical application of a ferric chloride solution was used to injure the vessel. Male Sprague-Dawley rats (375–450 g) were anesthetized with xylazine (20 mg/kg, s.c.) followed by ketamine HCl (100 mg/kg, s.c.). Animals were laid on a water blanket in which the circulated water was maintained at 37° C. The carotid artery was approached through a midline cervical incision. Careful blunt dissection was used to expose and isolate the vessel from the carotid sheath. A silk suture was pulled underneath the artery to lift the vessel to provide clearance to insert a thermocouple underneath it. Vessel temperature changes were monitored on a strip chart recorder that had an ink-writing timer. Small forceps were used to dip discs (3 mm dia) of Whatman No. 1 filter paper into a FeCl$_3$ solution (35%). The discs were cut to equal size using sharpened stainless steel tubing (3 mm i.d.) chucked in a drill press. A saturated disc was placed on each carotid artery above the thermocouple. The time between FeCl$_3$ application and the time at which temperature decreased abruptly was recorded as time to occlusion (TTO) of the vessel. The average time required for both vessels to occlude was used to represent TTO for each animal.

Test compounds were dissolved in isotonic saline. A syringe pump was used to infuse drug solutions starting 15 min before FeCl$_3$ application and continuing for 60 min after FeCl$_3$ application. Dose-response curves were plotted to determine the relationship between the log$_{10}$ of the infused doses and the TTO of the injured arteries. A comparative index of antithrombotic activity was determined from the curves by calculating the infusion dose required to maintain blood flow for 50 min (ED 50 min).

The association between vessel occlusion and the abrupt temperature decrease was established by simultaneously recording the temperature and blood flow on the same recorder. A pulsed Doppler flow probe was placed around the carotid artery proximal to the thermocouple. The probe recorded changes in flow velocity; therefore, it was installed at a point where thrombosis did not occur and the internal diameter of the vessel remained constant due to distention with fluid blood. Baseline temperature and flow velocity (determined with a Directional Pulsed Doppler Flowmeter, Model 545-C, University of Iowa Bioengineering) were recorded before application of 35% ferric chloride. Results were reported as percent change from initial baseline values (6 min before occlusion). The time at which vessel temperature decreased rapidly was arbitrarily established as zero and pre- and post-occlusion temperature and flow values were referenced from that point.

The following Table 3 contains the results obtained with test compounds in the above described chemically induced thrombus test in the rat.

TABLE 3

| Antithrombotic Activity vs. Arterial Thrombosis in the Rat | |
|---|---|
| Test Compound A(C=O) - of Formula 1 | ED$_{50}$[1] (mg/kg/h) |
| N-Boc-D-phenylglycyl | 2.9 |
| N-Boc-D-cyclohexylglycyl | 11.3 |
| N-Boc-D-1-naphthylglycyl | 6.4 |
| N-Boc-DL-1-naphthylglycyl | 5.5 |
| N-Boc-D-2-naphthylglycyl | NA[2] |

[1]ED$_{50}$ is the infusion dose required to maintain blood flow for 50 min.
[2]Not active at 4 mg/kg/h or at 7 mg/kg/h, the highest doses tested The compounds of the invention inhibit clot formation without appreciable interference with the bodies natural clot lysing ability e.g. the compounds have a low inhibitory effect on fibrinolysis.

The invention in one of its aspects provides a method for inhibiting the formation of blood clots in man and animals which comprises administering to said man or animal an effective clot inhibiting non-toxic dose of a compound represented by the formula 1. The anticoagulant compound is administered orally, parenterally e.g. by intravenous infusion (iv), intramuscular injection (im) or subcutaneously (sc). Preferably administration is carried out by iv infusion.

An effective clot inhibiting dose is between about 5 rag and about 1000 mg. The dose regime may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 10 mg/kg/h and preferably between about 0.05 mg/kg/h and about 1.0 mg/kg/h.

For oral administration a dose of a compound of the instant invention in the range of about 0.1 mg/kg to about 20 mg/kg can be administered one or more times per 24 hours. Preferably the dose is in the range of about 0.5 mg/kg to about 5 mg/kg and is administered up to 4 times per 24 hours. The instant compounds can be orally administered using standard forms such as tablets, capsules, and the like as provided below.

The method of this invention also is practiced in conjunction with a clot lysing agent e.g. tissue plasminogen activator (tPA), modified tPA, streptokinase or urokinase. In cases when clot formation has occurred and an artery or vein is blocked, either partially or totally, a clot lysing agent is usually employed. A compound of the invention can be administered along with the lysing agent or subsequent to its use to prevent the reoccurrence of clot formation.

In carrying out the method the use of a preferred compound of the invention is desirable. For example use is made of a preferred compound such as described hereinabove. Preferred peptides are N-Boc-D-phenylglycyl-L-prolyl-L-arginine aldehyde and N-methyl-D-phenylglycyl-L-prolyl-L-arginine aldehyde which are in salt form e.g. as sulfates or hydrochlorides. Especially preferred compounds of the invention for use in the method are N-(D-1,2,3,4-tetrahydroisoquinolin-1-carbonyl)-2-prolyl-2-arginine aldehyde sulfate.

The invention also provides pharmaceutical formulations for use in the above described therapeutic method. Pharmaceutical formulations of the invention comprise an effective clot inhibitory amount of a compound represented by the formula 1 and a pharmaceutically acceptable carrier. For oral administration the antithrombotic compound is formulated in gelatin capsules or tablets which may contain excipients such as binders, lubricants, disintegration agents and the like. The compound can be used in sustained release formulations to provide a payout of the compound over a period of time. For parenteral administration the antithrombotic is formulated in a pharmaceutically acceptable diluent e.g. physiological saline (0.9%), 5% dextrose, Ringer's solution and the like.

The antithrombotic compound of the invention can be formulated in unit dosage formulations comprising a dose between about 1 mg and about 1000 mg. Preferably the compound is in the form of a pharmaceutically acceptable salt such as for example the sulfate salt, acetate salt, hydrochloride or phosphate salt. An example of a unit dosage formulation comprises 5 mg of N-Boc-D-phenylglycyl-L-prolyl-L-arginine aldehyde sulfate salt in a 10 ml sterile glass ampoule. Another example of a unit dosage formulation comprises about 10 mg of N-methyl-D-phenylglycyl-L-prolyl-L-arginine aldehyde sulfate in 20 ml of isotonic saline contained in a sterile ampoule.

A preferred formulation is a unit dosage form comprising between 5 mg and 50 mg of N-(D-1,2,3,4-tetrahydroisoquinolin-1-carbonyl)-L-prolyl-L-arginine aldehyde sulfate in sterile ampoules.

The following Examples are provided to further describe the invention and are not to be construed as limitations thereof.

The Rf values in the following examples were determined by silica gel thin layer chromatography using Kieselgel 60F-254 (Merck, Darmstadt) in the following solvent systems:

(A) chloroform-methanol-acetic acid, 135:15:1, v:v:v
(B) ethyl acetate-acetic acid-absolute ethanol, 90:10:10, v:v:v
(C) chloroform-methanol-acetic acid, 90:30:5, v:v:v The analytical HPLC methods used in the examples were as follows:

Method 1. Waters 600E using a Vydac $C_{18}$ reversed-phase column of 0.46 cm×10 cm. The chromatogram was monitored on an LDC at 220 nM using a gradient of A=0.01M ammonium acetate and B=acetonitrile.

Method 2. Pharmacia FPLC using a PepRPC measuring 0.5 cm×5.0 cm. Monitoring was done on a Pharmacia UV-M at 214 nM using a gradient of either A=0.01M ammonium acetate or B=acetonitrile.

The abbreviations used herein have the following meanings.

Amino acids: Arg=arginine, Pro=proline, Phg=phenylglycine
Boc=t-butyloxycarbonyl
Bzl=benzyl
Cbz (or Z)=benzyloxycarbonyl
DCC=dicyclohexylcarbodiimide
DMF=dimethylformamide
DMSO=dimethylsulfoxide
FAB-MS=fast atom bombardment mass spectrum
FD-MS=field desorption mass spectrum
THF=tetrahydrofuran
TLC=thin layer chromatography

EXAMPLE 1

N-Boc-D-Phenylglycyl-L-Prolyl-L-Arginine aldehyde (Boc-D-Phg-Pro-Arg-H) hemisulfate 1) Boc-D-Phg-Pro-OBzl A solution of Boc-D-phenylglycine (15.0 g, 59.7 mmole) and proline benzyl ester hydrochloride (14.43 g, 59.7 mmole) in 60 ml of DMF was cooled to 0° C. and N,N-diisopropylethylamine (10.3 ml, 59.7 mmole) was added followed by 1-hydroxybenzotriazole hydrate (8.1 g, 59.7 mmole) and DCC (12.3 g, 59.7 mmole). The reaction mixture was stirred for 3 days at room temperature after which it was filtered and the filtrate was evaporated to an oil under vacuum. The oil was dissolved in 200 ml of ethyl acetate and 150 ml of water and after shaking the organic layer was separated, washed three times with 100 ml portions of 0.1N HCl, once with 150 ml of water, three times with 100 ml portion of 5% sodium bicarbonate and again with 150 ml of water. The washed organic solution was dried over $MgSO_4$ and then was evaporated under vacuum to provide 24.8 g of Boc-D-Phg-Pro-OBzl as a solid (95% of theory): TLC $R_f$(A) 0.75; FAB-MS 439 (M+).

2) Boc-D-Phg-Pro-OH

The Boc-D-Phg-Pro-OBzl product obtained as described above (24.5 g, 55.7 mmole) was dissolved in 40 ml of DMF and 225 ml of isopropyl alcohol and 1.0 g of 5% Pd on carbon catalyst were added to the solution. Nitrogen was bubbled into the reaction mixture via a gas dispersion tube and then hydrogen was bubbled through for 16 hours followed by a nitrogen purge for 5 minutes. The catalyst was filtered through a hyflo filter pad and the filtrate was evaporated to dryness under vacuum to yield a solid residue. The residue was crystallized from diethyl ether containing a small amount of ethyl acetate. There were obtained 10.35 g of the deesterified product. Boc-D-Phg-Pro (2), 53% yield: TLC $R_f$(A) 0.32; FAB-MS 349 (MH+);

$^1$H NMR (DMSO-d$_6$), δ 1.35 (s, 9H), 1.71–2.10 (m 4H), 3.10 (m, 1H), 3.74 (M, 1H), 4.20 (m 1H), 5.45 (d, 1H), 7.09 (d, 1H), 7.25–7.40 (m, 5H), 12.50 (bs, 1H).

3) Boc-L-Arg(Cbz)-OH

N-Boc-arginine hydrochloride (Boc-Arg-OH.HCl). (82.1 g, 250 mmole) was dissolved in 240 ml of 5N NaOH in a 3-necked round bottom flask. The solution was cooled to −5° C. and benzyl chloroformate (143 ml, 1.0 mole, 4 eq.) was added dropwise over 55 min while the pH of the mixture was maintained at 13.2–13.5 with 5N NaOH (250 ml). The reaction mixture was stirred for one hour at −5° C. after addition of the chloroformate was completed. The reaction mixture was diluted with 100 ml of water and 500 ml of diethyl ether and the aqueous layer was separated and extracted twice with 40 ml portions of diethyl ether. The aqueous layer was acidified to pH 3.0 with 3N H$_2$SO$_4$ (560 ml) and extracted with 550 ml of ethyl acetate. The separated aqueous layer was extracted once with ethyl acetate and the extract combined with the previous ethyl acetate extract. The combined extracts were washed with water, dried over MgSO$_4$ and evaporated to dryness under vacuum. The residue was triturated with ether and the precipitated product was filtered and dried. There were obtained 66.1 g of (3) Boc-Arg(Cbz)-OH (65% of theory): TLC $R_f$ (C) 0.43; FD-MS 408 (M+).

$^1$H NMR (CDCl$_3$), δ 1.42 (s, 9H), 1.61–1.91 (m, 4H), 3.23–3.41 (m, 2H), 4.17 (d, 1H), 5.21 (s, 2H), 5.62 (d, 1H), 7.30–7.42 (m, 6H), 8.37 (m, 1H),

4) Boc-Arg (Cbz)-Lactam

A solution of Boc-Arg(Cbz)-OH (3) prepared as described above (66.0 g, 0.162 mole) in 230 ml of dry THF was cooled to −10° C. in an ice-acetone bath. To the cold solution was added N-methylmorpholine (18.7 ml, 1.05 eq) followed by isobutyl chloroformate (22.5 ml, 1.05 eq) and the mixture was stirred for 5 minutes at −10° C. Next, triethylamine (23.5 ml, 1.05 eq) was added and the mixture was stirred for 1 h at −10° C. and at room temperature for 1 h. The reaction mixture was poured into one liter of an ice-water mixture and the product (4) precipitated. The precipitate was filtered, washed with cold water, dried under vacuum, and was crystallized from ethyl acetate. There was obtained 38.05 a (60% of theory) of the product 4, Boc-Arg(Cbz)-lactam: TLC $R_f$ (A) 0.77; FD-MS 391 (MH+).

$^1$H NMR (CDCl$_3$) δ 1.48 (s, 9H), 1.78–1.98 (m, 2H), 2.50 (m, 1H), 3.41 (m, 1H), 4.43 (m, 1H), 4.90 (m, 1H), 4.16 (s, 2H), 5.27 (m, 1H), 7.28–7.45 (m, 6H), 9.41 (m, 1H), 9.68 (m, 1H).

5) Arg(Cbz)-Lactam Trifluoroacetate salt.

Boc-Arg(Cbz)-lactam (4) (38.0 g, 0.097 mole) was mixed with 200 ml of trifluoroacetic acid containing 20 ml of anisole and the mixture was stirred at 0° C. for one hour. The reaction mixture was evaporated under vacuum without heating and 400 ml of diethyl ether were added to the residue. The resulting solid was filtered, washed with diethyl ether and dried under vacuum.

There were obtained 40.5 g of the product (5) trifluoroacetate salt: TLC $R_f$(C) 0.29; FD-MS 291 (MH+).

6) Boc-D-Phg-Pro-Arg(Cbz)-Lactam

To a solution of Boc-D-Phg-Pro (14.5 g, 41.6 mmole), prepared as described in part 2 above, in 80 ml of DMF cooled to −15° C. was added 4.6 ml of N-methylmorpholine followed by 5.4 ml of isobutyl chloroformate and the reaction mixture was stirred at −15° C. for two minutes.

In a separate flask TFA.Arg (Cbz) lactam (15.3 g, 37.8 mmole, prepared as described above in part 5), was dissolved in 30 ml of DMF, the solution cooled to 0° C. and 4.6 ml of N-methylmorpholine were added. After the solution was stirred at 0° C. for two minutes it was poured into the Boc-D-Phg-Pro solution prepared as described above. The reaction mixture obtained was stirred for 4 h at −15° C. and then was allowed to warm to room temperature overnight. A 5% solution of NaHCO$_3$ (5 ml) was added to the reaction mixture which was then evaporated under vacuum to provide an oil. The oil was dissolved in 175 ml of ethyl acetate and 150 ml of water were added. After shaking, the organic layer was separated, washed with 5% NaHCO$_3$ and water, dried over MgSO$_4$ and evaporated to dryness under vacuum to yield 23.0 g of Boc-D-Phg-Pro-Arg(Cbz) lactam (6) as an amorphous solid (98% yield). TLC $R_f$(A) 0.72. FAB-MS 621 (MH+).

7) Boc-D-Phg-Pro-Arg(Cbz)-H

The lactam (6) (23.0 g, 37 mmole), obtained as described in part 6 above was dissolved in 200 ml of dry THF and the solution cooled to −15° C. under a nitrogen atmosphere. To the cold solution was added dropwise over 10 min a 1M solution of lithium aluminum hydride in THF (37 ml, 37 mmole) and after addition was complete the reaction mixture was warmed to 0° C. and stirred for 1 h. A solution of 12 ml of THF and 12 ml of 0.5N H$_2$SO$_4$ was slowly added dropwise to the mixture over 10 min. The reaction mixture was diluted with 200 ml of ethyl acetate and 200 ml of water and after shaking, the organic layer was separated. The organic layer was washed 3 times with 150 ml portions of water, dried over MgSO$_4$ and evaporated to dryness under vacuum to yield 19.2 g (83% yield) of Boc-D-Phg-Pro-Arg(Cbz)-H. FAB-MS 623 (MH+). [α]$_D$=−66.1°, C=0.5, CHCl$_3$.

8) Boc-D-Phg-Pro-Arg-H hemisulfate

Boc-D-Phg-Pro-Arg(Cbz)-H (7) (18.2 g, 29.2 mmole) was dissolved in 100 ml of THF and 100 ml of water and 29.2 ml of 1N H$_2$SO$_4$ and 2 g of 10% Pd/C were added to the solution. Nitrogen was bubbled into the suspension for 5 min via a gas dispersion tube followed by hydrogen for 4 h. After the reduction was complete nitrogen was bubbled through again for 5 minutes. The reaction mixture was filtered through a hyflo pad to remove the catalyst and the filtrate was concentrated to a volume of 100 ml by evaporation under vacuum. To the aqueous concentrate were added 200 ml of n-butanol and the organic layer was separated from the aqueous layer. The aqueous was extracted three times with 100 ml portions of n-butanol and the extracts were combined and added to the organic layer. The organic layer was evaporated to dryness under vacuum, the residue triturated with diethyl ether/diisopropyl either, 1:1, v:v, and the solid filtered and dried under vacuum to yield 10.26 g of the crude product (8). The crude material was dissolved in 10% acetonitrile-water and the solution applied to a 7.5 cm×53 cm column of HP-20 resin previously equilibrated in 10% acetonitrile-water. The product was eluted from the columns by step-wise elution with increasing concentrations of acetonitrile in water (10% to 12% to 15%). Multiple fractions were collected and assayed for the product via reversed-phase HPLC. Fractions containing the product were pooled and evaporated to dryness to yield 5.42 g of the pure product, Boc-D-Phg-Pro-Arg-H hemisulfate, (53% yield): $[\alpha]_D = -125.6°$, C=0.5 CHCl$_3$; FAB-MS 489 (MH+); Retention Time on RP-HPLC (Method 2, 10-50% B over 45 min., time=32.3 min.

EXAMPLE 2

N-(t-Butyloxycarbonyl)-D-phenylglycyl-L-Prolyl-L-Arginine aldehyde (Boc-D-Phg-Pro-Arg-H) diacetate salt To a solution of Boc-D-Phg-Pro-Arg(Cbz)-H, prepared as described in part 7 of Example 1, (38.0 g, 61 mmole) in 500 ml of isopropyl alcohol containing 7.1 ml, (2 eq.) of acetic acid was added 2.0 g of 10% Pd on carbon catalyst. The mixture was purged with nitrogen via a gas dispersion tube for 5 min and then hydrogen was passed through the mixture for 24 h. After the reduction was complete nitrogen was passed through the mixture again for 5 min. The reaction mixture was filtered through a Hyflo pad to remove the catalyst and the filtrate was evaporated to dryness yielding 33.6 g of the crude product as an amorphous solid. The product was purified in 5 g lots over a 5 cm×25 cm column of Vydac C$_{18}$. The tripeptide product was eluted over 8 h with a gradient of 10–30% acetonitrile/0.01M ammonium acetate. Multiple fractions were collected and those fractions containing the product as shown by reversed phase HPLC were pooled and freeze dried. There were obtained 11.7 g (35% yield) of the title tripeptide having the following characteristics:

FAB-MS 489 (MH+) Amine acid analysis: Phg=1.07, Pro=0.94 $[\alpha]_D -108.9°$ (C=0.5, CHCl$_3$) Elemental Analysis calculated for C$_{28}$H$_{44}$N$_6$O$_9$: Theory: C, 55.25; H, 7.29; N, 13.81 Found: C, 55.52; H, 7.40; N, 13.93 Retention Time=31.9 min via HPLC Method 2; 10 to 50% B over 45 min.

The compounds characterized in the following Examples 3–4 were obtained by following the procedures described by Example 1 with the indicated naphthylglycine and p-hydroxyphenylglycine being substituted for the phenylglycine of Example 1.

EXAMPLE 3

N-Boc-D-1-naphthylglycyl-Pro-Arg-H diacetate $[\alpha]_D = +18.87°$, C=0.5, 50% acetic acid FAB-MS (MH+) 539 HPLC method 1, gradient: 20% to 60% B over 60 min. Retention time=42.0 min.

EXAMPLE 4

N-Boc-D-2-naphthylglycyl-Pro-Arg-H diacetate

HPLC method 2, gradient 30% to 60% B over 60 min. Retention time=18.0 min. Elemental analysis calculated for C$_{32}$H$_{46}$N$_6$O$_9$: Theory: C, 58.35; H, 7.04; N, 12.76 Found: C, 58.59, H, 6.83; N, 13.03

EXAMPLE 5

N-Boc-D-(4-hydroxyphenylglycyl)-Pro-Arg-H diacetate

HPLC method 2, gradient 10% to 40% B over 40 min. Retention time=26.5 min. Amino acid analysis: 4-hydroxyphenylglycine=0.99, proline=1.01.

EXAMPLES 6–23

The compounds listed in the following Table 4 were prepared by the coupling methods described by Example 1 when the indicated amino acid or substituted acetic acid [A(C=O)] was substituted for the D-phenylglycine used in Example 1. The compounds in Table 4 are acetate, hydrochloride or sulfate salt forms as indicated.

TABLE 4

| | A(C=O)—Pro—Arg—H | | | |
|---|---|---|---|---|
| Ex. No. | A(C=O)— | MS[1] | HPLC Method[2] No./Gradient | Retention Time (min) |
| 6 | N-Methyl-D-phenylglycyl | 403 | 1/10% - 50% B over 60 min. | 44.2 |
| 7 | N-Boc-DL-1-naphthlylglycyl | 539 | 1/5% - 50% B over 30 min. | 27.9 |
| 8 | N-Boc-D-(6-methoxy)-2-naphthylglycyl | 569 | 2/10% - 50% B over 45 min. | 42.2 |
| 9 | R(+)-α-Ethylphenylacetyl | 402 | 1/5% - 40% B over 60 min. | 22.1 |
| 10 | N-Boc-N-methyl-D-phenylglycyl | 503 | 2/5% - 50% B over 40 min. | 36.9 |
| 11 | R(+)-α-Methoxyphenylacetyl | 404 | 2/10% - 40% B over 40 min. | 21.0 |
| 12 | D-Phenylglycyl | 388 | 2/10% - 50% B over 45 min. | 13.6 |
| 13 | N-Boc-D-(4-methoxy)phenylglycyl | 519 | 2/10% - 45% B over 40 min. | 34.0 |
| 14 | N-Acetyl-D-(4-methoxy)phenylglycyl | 461 | 2/10% - 40% B over 40 min. | 19.0 |
| 15 | N-Boc-D-cyclohexylglycyl | 495 | 2/10% - 50% B over 40 min. | 36.5 |
| 16 | N-Boc-DL-(3,4-dichloro)phenylglycyl | 557 | 2/10% - 70% B over 60 min. | 40.5 |
| 17 | R(+)-α-Methylphenylacetyl | 388 | 2/10% - 50% B over 45 min. | 21.9 |
| 18 | S(−)-α-Methylphenylacetyl | 388 | 2/10% - 50% B over 45 min. | 22.6 |
| 19 | N-Boc-D-2-thienylglycyl | 495 | 1/10% - 60% B over 60 min. | 23.8 |
| 20 | N-Boc-D-(4-fluoro)phenylglycyl | 507 | 2/10% - 50% B over 60 min. | 38.4 |
| 21 | N-Boc-DL-(4-fluoro)phenylglycyl | 507 | 2/10% - 50% B over 60 min. | 37.3 |
| 22 | N-Boc-1,2,3,4-tetrahydroisoquinolin-1-carbonyl | 515 | 1/20% to 60% B over 60 min. | 49.0 |
| 23 | D-1,2,3,4-Tetrahydroisoquinolin-1-carbonyl | 415 | 2/5% to 50% B over 60 min. | 30.6 |
| 24 | D-1,2,3,4-Tetrahydroisoquinolin-3-carbonyl | 415 | 2/5% to 50% B over 60 min. | 26.4 |
| 25 | D-Perhydroisoquinolin-1-carbonyl | 421 | 2/5% to 50% B over 60 min. | 22.2 25.9 |
| 26 | N-Boc-DL-(3-trifluoromethyl)phenylglycyl | 557 | 2/5% to 50% B over 60 min. | 51.5 |

[1]FAB-MS(MH')
[2]The HPLC method is that described above

EXAMPLE 24

D-1,2,3,4-Tetrahydroisoquinolin-1-carbonyl-L-Prolyl-L-Arginine Aldehyde Sulfate To a solution of isoquinoline-1-carboxylic acid (12.5, 0.072 mole) in 185 ml of glacial acetic acid was added 2 g of platinum oxide and the suspension was hydrogenated at room temperature under 60 psi hydrogen pressure in a Parr hydrogenation apparatus for 24 h. The reaction mixture was filtered though a filter pad (Celite) to remove the catalyst and the filtrate was evaporated to dryness in vacuo. The solid residue was triturated with water, filtered and dried to yield 8 g (63% yield) of DL-1,2,3,4-tetrahydroisoquinolin-1-carboxylic acid. FD-Mass spectrum 178 (MH+);

$^1$H NMR (DMSO-d$_6$): δ 2.80–3.00 (m, 3H), 3.15 (m, 1H), 3.30–3.40 (m, 2H), 7.05–7.25 (m, 4H), 7.70 (m, 1H).

The product (7.08 g, 0.04 mole) was dissolved in 2N NaOH (40 ml, 0.08 mole) and 40 ml of t-butyl alcohol and 10.5 g (0.048 mole) of di-tert-butyl dicarbonate were added to the solution. After stirring for 24 h at room temperature the bulk of the t-butyl alcohol was evaporated from the reaction mixture. The resulting aqueous solution was extracted with diethyl ether, the aqueous layer separated and acidified with 2N HCl to pH 2.0. The acidified aqueous phase was extracted with ethyl acetate, the extract dried over MgSO$_4$ and evaporated to dryness in vacuo. The residual oil was dissolved in diethyl ether and 7.9 ml (0.04 mole) of dicyclohexylamine was added to the solution. After standing at 4° C. for 4 h the precipitate of the dicyclohexylamine salt of N-Boc-DL-1,2,3,4-tetrahydroisoquinolin-1-carboxylic acid was filtered, washed with diethyl ether and dried in vacuo to yield 15.7 g (86% yield) of the pure salt. FD-Mass spectrum 459 (MH+).

Elemental analysis calculated for C$_{27}$H$_{42}$N$_2$O$_4$: Theory: C, 70.71; H, 9.23; N, 6.11 Found: C, 71.07; H, 9.37; N, 5.87

The Boc protected derivative (73.4 g, 160 mmole) was suspended in 200 ml of ethyl acetate and the suspension was washed with 1.5N citric acid and water, was dried over MgSO$_4$ and evaporated to dryness under vacuum. The residual oil was dissolved in ethyl acetate, the solution cooled to 0° C. and 2,4,5-trichlorophenol (31.6 g, 160 mmole) was added to the solution followed by DCC (33 g, 160 mmole). The reaction mixture was stirred for one hour at 0° C. and at room temperature (1.5 h). The reaction mixture was cooled to 0° C. the precipitate filtered and the filtrate evaporated to dryness under vacuum. The residual oil was dissolved in 100 ml of pyridine and proline (18.42 g, 160 mmole) and triethylamine (22.3 ml, 160 mmole) were added to the solution. After stirring at room temperature (24 h) the reaction mixture was evaporated to dryness under vacuum. The residue was dissolved in ethyl acetate, water was added and the pH adjusted to 9.5 with 2N NaOH. The aqueous layer was separated, acidified to pH 2.0 with 2N HCl, and extracted with ethyl acetate. The extract was dried over MgSO$_4$, filtered and evaporated to dryness under vacuum. The oil residue was dissolved in methylene chloride and ethyl acetate. After standing at 4° C. for 4 h a precipitate formed in the solution, was filtered, washed with ethyl acetate and recrystallized from methylene chloride/ethyl acetate. The solid product, Boc-D-1,2,3,4-tetrahydroisoquinolin-1-carbonyl-L-proline (Boc-D-1-Tiq-Pro-OH), was dried under vacuum to give 19.6 g, 33% yield of the pure product, TLC R$_f$(A) 0.44; FAB-MS, 375 (MH+);

Elemental analysis calculated for C$_{20}$H$_{26}$N$_2$O$_5$; Theory: C, 64.15; H, 7.00; N, 7.48 Found: C, 63.26; H, 6.98; N, 7.52 [α]$_D$= +43.14°, C=0.5, methanol.

In a first flask, Boc-D-1-Tiq-Pro (17.8 g, 47.5 mmole) was dissolved in 100 ml of DMF, the solution cooled to −15° C. and 5.3 ml (52.3 mmole) of N-methylmorpholine and 6.2 ml (47.5 mmole) of isobutylchloroformate were added. The mixture was stirred at −15° C. for two min.

In a second flask, the Cbz protected arginine lactam as the trifluoroacetate salt [Arg(Z)-Lactam.TFA], (19.2 g, 47.5 mmole) was dissolved in 40 ml of DMF, the solution cooled to 0° C., and 5.3 ml (52.3 mmole) of N-methylmorpholine were added. The mixture was stirred for 2 min at 0° C. before being added to the first flask. The reaction mixture was stirred for 4 h at −15° C., then was slowly warmed to room temperature overnight and 5 ml of 5% NaHCO$_3$ was added. The reaction mixture was evaporated under vacuum to provide an oil. The oil was dissolved in 175 ml of ethyl acetate and 150 ml of water were added to the solution. The organic layer was separated, washed with 5% NaHCO$_3$, water, 0.1N HCl and with water again before drying over MgSO$_4$. The washed and dried solution was evaporated under vacuum to dryness to yield 24.3 g (79% yield) of the product, Boc-D-1-Tiq-Pro-Arg(Z) lactam, as an amorphous solid. TLC R$_f$ (A) 0.71 FAB-MS 647 (MH+) [α]$_D$= −32.8° C=0.5 chloroform The Arg(Z) lactam product obtained above (23.4 g, 36.2 mmole) was dissolved in 300 ml of dry THF and the solution placed under N$_2$. The solution was cooled to −60° C. and 37 ml lithium aluminum hydride 1M in THF (37 mmole) was added dropwise to the cold solution over 30 min. After addition was completed the mixture was stirred at −60° C. for 30 min, and a solution of 20 ml of THF and 20 ml of 0.5N H$_2$SO$_4$ was added dropwise over 10 min. The reaction mixture was diluted with 400 ml of ethyl acetate and 400 ml of water were added. The organic layer was separated, washed twice with 150 ml portions of water and dried over MgSO$_4$. The washed and dried organic layer was evaporated under vacuum to yield 21 g (89% yield) of the product, Boc-D-1-Tiq-Pro-Arg(Z)-H, as an amorphous solid. TLC R$_f$(A) 0.28.

The Arg(Z)-H product obtained as described aboved was hydrogenated as follows to remove the Cbz protecting group. The product (18.1 g, 27.9 mmole) was dissolved in 200 ml of THF and 80 ml of water and 28 ml of 1N H$_2$SO$_4$ and 3.0 g of 5% Pd-on-carbon were added. Nitrogen was bubbled through the suspension via a gas dispersion tube for 5 min. followed by hydrogen for 5 h and thereafter nitrogen for 5 min. The catalyst was filtered and the filtrate concentrated to a volume of 100 ml. The concentrate was diluted with 200 ml of n-butanol and the layers separated. The aqueous layer was extracted three times with 100 ml portions of n-butanol and the extracts were combined with the organic layer. The organic layer was evaporated under vacuum, and the reaction product residue triturated with diethyl ether:diisopropyl ether, 1:1, v:v, the solid was filtered and dried under vacuum to give 11.08 g of crude product.

The product was purified and obtained as the sulfate salt as follows. The crude product obtained as described above was dissolved in 20 ml of water and 20 ml of 10N H$_2$SO$_4$. The solution was heated at 50° C. for 25 min., cooled to room temperature and the pH of the solution was adjusted to 4.0 with Bio-Rad AG1-X8 resin (hydroxide form). The resin was separated from the solution by filtration and the solution was lyophilized to yield 8.44 g of the crude product as the sulfate salt, D-1-Tiq-Pro-Arg-H.H$_2$SO$_4$.

The sulfate salt (4.2 g) was dissolved in 0.01% H$_2$SO$_4$ and the solution applied to two 5 cm×25 cm HPLC reversed phase columns (Vydac C$_{18}$ resin) in series. A gradient of increasing concentrations of acetonitrile (2% to 10%) was used to elute the product salt. Fractions were collected and pooled on the basis of analytical RP-HPLC profile. The pH of the combined fractions was adjusted to 4.0 using AG1-X8 resin (Bio-Rad analytical anion exchange resin of 50-100 mesh) in the hydroxy cycle. The solution was filtered to remove the resin and the filtrate was lyophilized. There were obtained 2.4 g (57% of theory) of the purified product. FAB-MS 415 (MH+) [α]$_D$=−76.12°, C=0.5/0.01N H$_2$SO$_4$ Amino acid analysis: Pro, 0.92; Tiq, 1.00 Elemental analysis calculated for C$_{21}$H$_{32}$N$_6$O$_7$S: Theory: C, 49.21; H, 6.29; N, 16.29; S, 6.26 Found: C, 51.20; H, 6.17; N, 16.88; S, 5.37.

EXAMPLE 25

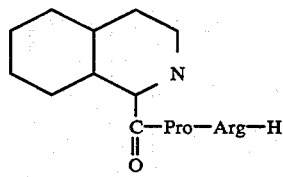

[4aR, 8aR]
Perhydroisoquinolin-1-carbonyl-L-propyl-L-arginal

The R$_f$ values in the examples are determined by silica gel thin layer chromotography (Kieselgel 60 F-254) in the following systems:
  (A) Chloroform-Methanol-Acetic Acid 135:15:1
  (B) Ethylacetate-Acetic Acid-Absolute Alcohol 90:10:10
  (C) Chloroform-Methanol-Acetic Acid 90:30:5

DL-1,2,3,4,6,7,8-Perhydro-1-isoquinolinecarboxylic acid (1)

A solution of 1-isoquinolinecarboxylic acid (50 g, 0.288 mol) in EtOH(150 mL) and 60 ml of 5N HCl was reacted with 5% Rh/Al$_2$O$_3$ (14 g) at 750 psi of hydrogen in a high pressure apparatus at 50° C. for 17 h. The reaction mixture was filtered through a Celite pad, and the filtrate was concentrated in vacuo. The solid triturated with water filtered and dried to give the title compound (30 g, 48%) FD-MS 184 (MH+).

Cbz-DL-1,2,3,4,6,7,8-Perhydro-1-isoquinolinecarboxylic acid (2)

DL-1-Piq (1) (30.2 g, 137 mmol) was dissolved in tetrahydrofuran (150 mL) and water (150 mL). The pH of the solution was adjusted to 9.8 with 5N NaOH and benzyl chloroformate (21.6 mL, 151 mmol) was added dropwise and the pH maintained at 9.5 with 2N NaOH. The reaction was stirred for an additional 2 h at room temperature. The organic solvent was evaporated in vacuo, diethylether (150 mL) and water (50 mL) was added to the residue. The aqueous layer separated, the pH of the solution was adjusted to 2.5 with 5N HCl and ethyl acetate (200 mL) was added. The organic layer was separated and dried (MgSO$_4$) the filtrate was concentrated in vacuo to give a clear oil. The oil was dissolved in diethylether (150 mL) and the solution allowed to stand at room temperature (24 h). The precipitate filtered and dried to give the title compound (32 g, 75%) FD-MS 318 (MH+).

Cbz-DL-1,2,3,4,6,7,8-Perhydro-1-isoquinolinecarboxyl-L-Prolyl-t-butylester (3)

Cbz-DL-1-Piq (2) (31.8 g, 100 mmol) was dissolved in DMF (100 mL) and cooled to 0° C. To the reaction was added Proline-t-butylester (17.1 g, 100 mmol), 1-hydroxybenzotriazole (13.5 g, 100 mmol), and DCC (20.6 g, 100 mmol). The reaction was stirred for 3 h at 0° C. and 24 h at room temperature. The reaction precipitate was filtered and the filtrate concentrated in vacuo to an oil. The oil was dissolved in EtOAc (200 mL) and water (100 mL). The organic layer was separated, washed with 1N NaHCO$_3$, water, 1.5N citric acid, and water. The organic layer was dried (MgSO$_4$), and the filtrate evaporated to an oil which was dried to give the title compound (47.0 g, 100%) FAB-MS 470 (MH+); TLC R$_f$(A) 0.77.

Cbz-D-1,2,3,4,6,7,8-Perhydro-1-isoquinolinecarboxyl-L-Proline (4)

Cbz-DL-1-Piq-Pro-O-t-Bu (3) (47.0 g, 100 mmole) was placed in a R.B. flask containing trifluoroacetic acid (100 ml), CH$_2$Cl$_2$ (35 mL), anisole (5 ml) and stirred at room temperature (1 h). The reaction was concentrated in vacuo without heating, diethylether (100 ml), and water (100 mL) was added. The pH of the solution was adjusted to 9.8 with 5N NaOH. The aqueous layer separated, the pH of the solution was adjusted to 2.5 with 5N HCl and ethyl acetate (200 mL) was added. The organic layer was separated and dried (MgSO$_4$) the filtrate was concentrated in vacuo to give a clear oil. The oil was dissolved in diethylether (700 mL) and L(−) alphamethylbenzylamine added to the solution. The solution was allowed to stand at room temperature for 5 days. The resulting solid was filtered washed with diethylether. The filtrate was washed with 1.5N citric acid, and water. The organic layer was dried (MgSO$_4$), and the filtrate evaporated to an oil. The oil was dissolved diethylether (400 mL) and allowed to stand at room temperature (48 h). The resulting solid was filtered, washed with diethylether, and dried to give the title compound (5.86 g, 36%) FAB-MS 415 (MH+); TLC R$_f$(A) 0.47; [α]$_D$=−34.2° (C=0.5 MeOH)

Boc-Arg(Cbz)-Lactam (5) was prepared as described in Example 1.

HCl-Arg(Cbz)-Lactam (6)

A solution of HCl (g) saturated in EtOAc (7.2 L) was added dropwise over 30 min. to a solution of Boc-Arg(Z)-Lactam (5) (641 g, 1.64 mol) dissolved in CH$_2$Cl$_2$(3 L) at 10° C. temperature over 3 h. Diethyl ether (12 L) was added and the precipitate was filtered, washed with diethyl ether, and dried in vacuo to give 580 g of the title compound (108% of theory): TLC R$_f$ (C) 0.29; FD-MS 291 (MH+).

Cbz-D-1-Piq-Pro-Arg(Z)-Lactam (7)

In flask 1 Cbz-D-1-Piq-Pro (4) (5.4 g, 13 mmole) was dissolved in DMF (75 ml), cooled to −15° C. and N-methylmorpholine (1.5 ml, 13 mmole) was added followed by isobutylchloroformate (1.7 ml, 13 mmole). The rxn mixture was stirred at −15° C. for 2 min.

In flask 2 HCl.Arg(Cbz)-Lactam (6) (4.2 g, 13 mmole) was dissolved in DMF (50 ml), cooled to 0° C. and DIEA (6.7 ml, 39 mmole) was added to the solution. The reaction mixture was stirred at 0° C. for 2 min.

The contents of flask 2 was added to flask 1 and the reaction mixture was stirred for 4 h (−15° C.). The reaction mixture was slowly warmed to room temperature overnight and 5% NaHCO₃ (5 ml) was added. The reaction solvent was removed in vacuo and EtOAc (175 ml), water (150 ml) was added to the oil. The organic layer was separated, washed with 5% NaHCO₃, water, 1.5N citric acid, and water. The organic solution was dried (MgSO₄) and concentrated to dryness in vacuo to an amorphous solid. The crude solid was chromatographed over silica gel. A gradient system consisting of (A) CHCl₃ and (B) EtOAc was used to elute the pure compound. The gradient used was an increasing concentration of EtOAc from 0% to 50%. Fractions were collected and pooled on the basis of TLC profile. The combined fractions were concentrated in vacuo to give an amorphous solid of the title compound (6.1 g, 76%): TLC $R_f$(A) 0.66; FAB-MS 687 (MH+); $[\alpha]_D = -34.1°$ (C=0.5 THF)

Cbz-D-1-Piq-Pro-Arg(Cbz)-H (9)

Cbz-D-1-Piq-Pro-Arg(Cbz)-Lactam (8) (6.1 g, 8.9 mmole) was dissolved in dry THF (100 ml) and placed in a R.B. flask under a N₂ atmosphere. The reaction cooled to −78° C. and lithium aluminium hydride 1M in THF (9.0 ml, 9 mmole) was added dropwise. The reaction was stirred at −78° C. for 30 min. and a solution of 5 ml of THF and 5 ml of 0.5N H₂SO₄ was added dropwise to the reaction. The reaction was diluted with EtOAc (200 ml), water (100 ml) and the EtOAc layer separated. The organic solution was dried (MgSO₄), concentrated to dryness in vacuo to an amorphous solid of the title compound (5.7 g, 93% of theory): TLC $R_f$ (A) 0.39; FAB-MS 689 (MH+)

D-1-Piq-Pro-Arg-H 2HCl (10)

Cbz-D-1-Piq-Pro-Arg(Cbz)-H (9) (5.7 g.8.3 mmole) was dissolved in EtOH (125 ml) and 1N HCl (21 ml). To the reaction was added 5% Pd/C (3.0 g.) and water (75 mL). Nitrogen was bubbled into the reaction through a gas dispersion tube for 5 min. followed by hydrogen for 2 hrs., and nitrogen for 5 min. The catalyst was removed by filtration through a hyflo pad and the filtrate concentrated in vacuo to 20 mL. An additional 50 mL of H₂O was added to the reaction and pH of solution adjusted to 4.0 with BioRad AG1-X8 resin (hydroxide form). The resin was removed by filtration and the solution lyophilized to give pure title compound (3.68 g, 92%): FAB-MS 421 (MH+); $[\alpha]_D = -86.3°$ (C=0.5/0.01N HCl); elemental analysis (calcd) C₂₁H₃₆N₆O₃.2HCl.2H₂O: C, 47.68; H, 8.00; N, 15.88. Found: C, 47.68, H, 7.54, N, 15.84.

EXAMPLE 27

Synthesis of D-1,2,3,4,6,7,8-Perhydroisoquinolin-3-carbonyl-L-prolyl-L-arginal (sulfate)

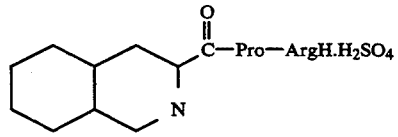

D-1,2,3,4-Tetrahydro-3-isoquinolinecarboxylic acid (1)

D-Phe (50 g, 302 mmol) was reacted with 37% solution of formaldehyde (120 mL) and conc. HCl (380 mL) at reflux temperature. After 30 min. of reflux an additional 50 mL of formaldehyde was added and reaction refluxed for 3 h. The reaction cooled to −10° C. and the precipitate filtered. The solid was dried in vacuo to give the title compound (24.2 g, 45%) FD-MS 178 (MH+).

D-1,2,3,4,6,7,8-Perhydro-3-isoquinolinecarboxylic acid (2)

A solution of D-1,2,3,4-tetrahydro-3-isoquinolinecarboxylic acid (1) (17 g, 96 mmol) in water (200 mL) and 20 ml of 5N HCl was reacted with 5% Rh/Al₂O₃ (8.5 g) at 2000 psi in a high pressure apparatus at 120° C. for 16 h. The reaction mixture was filtered through a Celite pad, and the filtrate was freeze dried to give the title compound (21 g, 100%) FD-MS 184 (MH+).

Cbz-D-1,2,3,4,6,7,8-Perhydro-3-isoquinolinecarboxylic acid (3)

D-3-Piq (2) (21.0 g, 95.8 mmol) was dissolved in tetrahydrofuran (75 mL) and water (50 mL). The pH of the solution was adjusted to 10.0 with 5N NaOH and benzyl chloroformate (16.4 mL, 115 mmol) was added dropwise and the pH maintained at 9.5 with 2N NaOH. The reaction was stirred for an additional 1 h at room temperature. The organic solvent was evaporated in vacuo, diethylether (100 mL) and water (50 mL) was added to the residue. The aqueous layer separated, the pH of the solution was adjusted to 3.0 with 3N HCl and ethyl acetate (250 mL) was added. The organic layer was separated and dried (MgSO₄) the filtrate was concentrated in vacuo to give a clear oil of the title compound (25.8 g, 85%) FD-MS 318 (MH+); $[\alpha]_D = -5.1°$ (C=0.5 MeOH)

Cbz-D-1,2,3,4,6,7,8-Perhydro-3-isoquinolinecarboxyl-L-Prolyl-t-butylester (4)

Cbz-D-3-Piq (3) (17.2 g, 54 mmol) was dissolved in DMF (50 mL) and cooled to 0° C. To the reaction was added Proline-t-butylester (9.2 g, 54 mmol), 1-hydroxybenzotriazole (7.3 g, 54 mmol), and DCC (11.1 g, 54 mmol). The reaction was stirred for 3 h at 0° C. and 24 h at room temperature. The reaction precipitate was filtered and the filtrate concentrated in vacuo to an oil. The oil was dissolved in EtOAc (200 mL) and water (100 mL). The organic layer was separated, washed with 1N NaHCO₃, water, 1.5N citric acid, and water. The organic layer was dried (MgSO₄), and the filtrate evaporated to an oil which was dried to give the title compound (23.8 g, 94%) FAB-MS 471 (MH+); TLC $R_f$(A) 0.73; $[\alpha]_D = -40.0°$ (C=0.5 MeOH)

Cbz-D-1,2,3,4,6,7,8-Perhydro-3-isoquinolinecarboxyl-L-Proline (5)

Cbz-D-3-Piq-Pro-O-t-Bu (4) (31.2 g, 66.3 mmole) was placed in a R.B. flask containing trifluoroacetic acid (100 ml), anisole (5 ml), and stirred at room temperature (1 h). The reaction was concentrated in vacuo without beaming, diethylether (150 ml), and water (100 mL) was added. The pH of the solution was adjusted to 9.8 with 5N NaOH. The aqueous layer separated, the pH of the solution was adjusted to 2.8 with 3N HCl and ethyl acetate (200 mL) was added. The organic layer was separated and dried (MgSO₄) the filtrate was concentrated in vacuo to give a clear oil. The oil was dissolved in diethylether (300 mL) and the solution was allowed to stand at room temperature (24 h). The resulting solid was filtered washed with diethylether, and dried to give the title compound (13.5 g, 49%) FAB-MS 415 (MH+); $[\alpha]_D = -57°$ (C=0.5 MeOH); elemental analysis (calcd) C₂₃H₃₀N₂O₅: C, 66.65; H, 7.29; N, 6.76. Found: C, 66.90, H, 7.33, N, 6.81.

PCHEM DATA ON FINISHED COMPOUND

D-3-(cis)Piq-Pro-H.H₂SO₄

FAB-MS 421 (MH+); $[\alpha]_D = -41°$ C=0.5/0.01N H₂SO₄; elemental analysis (calcd) $C_{21}H_{36}N_6O_3 \cdot H_2SO_4 \cdot 3H_2O$: C, 44.04; H, 7.74; N, 14.68.

EXAMPLE 28

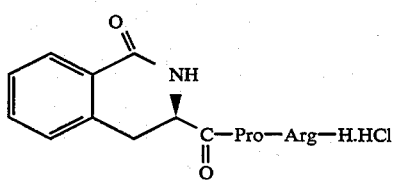

Synthesis of D-1,2,3,4-tetrahydroisoquinolin-1-keto-3-carbonyl-L-prolyl-L-arginine aldehyde (hydrochloride)

Acetamido-diethyl-2-carboxyethylbenzyl malonate (1)

Ethyl-2-methylbenzoate (82 mL, 510 mmol) was dissolved in carbontetrachloride (2500 mL) and stirred at room temperature. To the solution was added N-bromosuccinimide (100 g, 560 mmol), 2,2'-azobis(2-methylpropionitrile) (600 mg) and the reaction was refluxed (24 h). The reaction mixture was cooled to room temperature and the precipitate filtered. The filtrate was concentrated to dryness in vacuo to give a clear oil. The oil was dissolved in EtOH (100 mL) and added dropwise to a stirred solution containing sodium (10 g, 460 mmol), EtOH (500 mL), and diethylacetamido-malonate (100 g, 460 mmol). The reaction was refluxed (24 h). The reaction solvent was concentrated in vacuo to a solid. The solid was dissolved in EtOAc (500 mL), water (100 mL), the organic layer was separated, washed with water, and dried (MgSO₄). The filtrate evaporated to an oil. The oil was triturated with petroleum ether to give the title compound (138.8 g, 72%):MP=42-62

DL-1,2,3,4-Tetrahydro-3-carboxy-1-keto-isoquinoline (2)

A suspension of acetamido-diethyl-2-carboxyethylbenzyl malonate (1) (138.8 g, 365 mmol) in 6N HCl (2000 mL) was refluxed (20 h). The reaction was cooled to 0° C. and the precipitate was filtered. The crude solid was recrystallized from EtOH-water to give the title compound (42.3 g, 66%) MP=247°-252° C.; elemental analysis (calcd) $C_9H_8NO_3$: C, 62.82; H, 4.74; N, 7.33. Found: C, 63.04, H, 4.76, N, 7.23.

D-3-Tiq(1 keto)-Pro-OBzl (3)

A solution of DL-1,2,3,4-Tetrahydro-3-carboxy-1-keto-isoquinoline (2) (9.6 g, 50 mmol) in DMF (50 mL) was cooled to 0° C. To the reaction was added Proline-benzylester (12.1 g, 50 mmol), diisopropylethylamine (8.7 mL, 50 mmol), 1-hydroxybenzotriazole (6.8 g, 50 mmol), and DCC (10.3 g, 50 mmol). The reaction was stirred for 2 h at 0° C. and 24 h at room temperature. The reaction precipitate was filtered and the filtrate concentrated in vacuo to an oil. The oil was dissolved in EtOAc (200 mL) and water (100 mL). The organic layer was separated, washed with 1N NaHCO₃, water, 1.5N citric acid, and water. The organic layer was dried (MgSO₄), and the filtrate evaporated to a crude oil of the title compound (18 g). The crude solid was chromatographed over silica gel. A gradient system consisting of (A) hexane and (B) EtOAc was used to elute the pure compound. The gradient used was an increasing concentration of EtOAc from 0% to 100%. Fractions were collected and pooled on the basis of TLC profile. The combined fractions were concentrated in vacuo to give an amorphous solid of the title compound (6.2 g, 33%): TLC $R_f$ (A) 0.55; FAB-MS 379 (MH+); $[\alpha]_D = -68.7°$ (C=0.5 MeOH).

D-3-Tiq(1-keto)-Pro-OH (4)

A solution of D-3-Tiq(1 keto)-Pro-OBzl (3) (6.0 g, 15.9 mmole) in isopropyl alcohol (80 ml) was stirred at room temperature. The reaction was hydrogenated in the presence of 5% Pd/C catalyst (1.0 g) at ambient temperature and pressure. After the reaction was completed, the catalyst was removed by filtration and the filtrate concentrated in vacuo to give crude title compound. The solid was crystallized from hot EtOAc to give the title compound (3.6 g, 78%): $[\alpha]_D = -49.2°$ (C=0.5/MeOH). FAB-MS 429 (MH+); elemental analysis (calcd) $C_{21}H_{29}N_6O_4Cl$: C, 54.25 H, 6.29; N, 18.07. Found: C, 3.99, H, 6.04, N, 17.97.

EXAMPLE 29

Synthesis of Nᵅ-ethylcarbamate-1-amino-1-cyclohexane-carbonyl-L-prolyl-L-arginine Aldehyde (Hydrochloride)

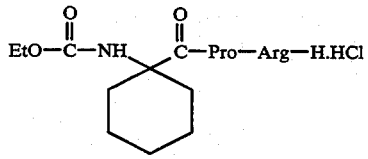

Nᵅ-ethylcarbamate-1-aminocyclohexane-1-carboxylic acid (1)

A suspension of 1-amino-1-cyclohexanecarboxylic acid (10 g, 69.8 mmol) in anhydrous THF (250 mL) was added to bis(trimethylsilyl)acetamide (21.3 g, 104.7 mmol), and stirred for 1 h at room temperature under an inert atmosphere. The reaction was cooled (0° C.) and DIEA (9.0 g, 69.8 mmol) was added. To the reaction was added a solution containing ethyl chloroformate (7.6 g, 69.8 mmol) and THF (20 mL) dropwise. The reaction was stirred at 0° C. for 3 h, warmed to room temperature, and diluted with water (100 mL). The organic solvent was evaporated in vacuo, diethylether (150 mL) and 1N NaOH (50 mL) was added to the residue. The aqueous layer separated, the pH of the solution was adjusted to 2.0 with 5N HCl and ethyl acetate (200 mL) was added. The organic layer was separated and dried (Na₂SO₄) the filtrate was concentrated in vacuo to give a white solid of the title compound (14.6 g, 97%) ¹HNMR (CDCl₃) d 1.20-2.15 (m, 13H), 4.0-4.20 (q, 2H), 5.10 (bs, 1H).

Nᵅ-ethylcarbamate-1-aminocyclohexane-1-carbonyl-Pro-Arg(Z)-Lactam (2)

Prepared as previously described as an amorphous solid: FAB-MS 585 (MH+); elemental analysis (calcd) $C_{29}H_{40}N_6O_7$: C, 59.57; H, 6.90; N, 14.37. Found: C, 59.80, H, 7.02, N, 14.32.

Nᵅ-ethylcarbamate-1-aminocyclohexane-1-carbonyl-Pro-Arg(Z)-H (3)

A solution of Nᵅ-ethylcarbamate-1-aminocyclohexane-1-carbonyl-Pro-Arg(Z)-Lactam (2) (6.0 g, 10.3 mmole) was dissolved in dry THF (100 ml) under an inert atmosphere and cooled (−25° C.). To the reaction was added Lithium tri-tert-butoxyaluminohydride 1M in THF (20.5 ml, 20.5 mmole) dropwise and the reaction stirred for 3.5 h at −25° C. The reaction was poured slowly into a flask containing 1N HCl (100 mL). The reaction was extracted with THF/hexane (1:1), twice with EtOAc (200 ml), and twice with CHCl₃/isopropyl alcohol (3:1). The EtOAc and CHCl₃ layers were combined and dried (Na₂SO₄). The filtrate concentrated to dryness in vacuo to an amorphous solid of the title compound (6.0 g, 100%).

N$^\alpha$-ethylcarbamate-1-aminocyclohexane-1-carbonyl-Pro-Arg-H HCl (4)

Prepared as previously described as a white solid. FAB-MS 453 (MH+); elemental analysis (calcd) $C_{21}H_{37}N_6O_5Cl$: C, 51.58 H, 7.63; N, 17.18, Cl, 7.25. Found: C, 51.83, H, 7.61, N, 17.18, Cl, 7.52; $[\alpha]_D = -65.1°$ (C=0.5/0.01N HCl).

EXAMPLE 30

Synthesis of N$^\alpha$-acetyl-1-aminocyclohexane-1-carbonyl-L-prolyl-L-arginine Aldehyde (Hydrochloride)

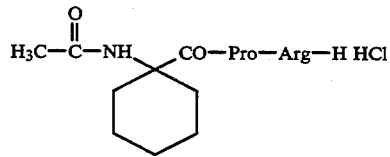

The title compound was prepared using standard procedures described herein starting with 1-amino-1-cyclohexanecarboxylic acid. FAB-MS 423 (MH+); elemental analysis (calcd) $C_{20}H_{35}N_6O_4Cl$·1.5 H₂O: C, 49.42 H, 7.67; N, 17.29. Found: C, 49.12, H, 7.71, N, 17.16.

EXAMPLE 31

Preparation of N-methyl-D-cyclohexylglycyl-L-prolyl-arginal.hydrochloride

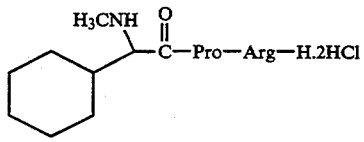

N-Cbz-D-cyclohexylglycine (1)

To a stirring solution of D-cyclohexylglycine (20.3 g, 129 mmol) in 5N aqueous NaOH (26 mL) and water (100 mL), at 0° C., were simultaneously added dropwise via separate additional funnels; A) benzyl chloroformate (493.8 mL, 194 mmol) and B) 5N aqueous NaOH (39 mL). The pH was continuously monitored to make sure that the solution remained basic. After complete addition the cold bath was removed and the solution continued to stir for 1 h. The aqueous phase was then extracted three times with ether (300 mL). The combined ether phases were washed twice with water (200 mL) and the ether phase was then refrigerated overnight. The next morning, the solution was filtered to give white crystals (14 g, 37%).

N-Cbz-D-cyclohexylglycyl-proline (2)

To a solution N-Cbz-D-cyclohexylgicine (13.9 g, 48 mmol), proline benzyl ester.HCl (11.5 g, 48 mmol), 1-hydroxybenzotriazole (6.5 g, 48 mmol), and N,N-diisopropylethylamine (29 mL, 167 mmol) in dichloromethane (200 mL) at 0° C. was added 1-(3-dimethylaminopropyl)-3-ethylcarbodiimide (10.1 g, 53 mmol). The cold bath was then removed and the solution warmed to room temperature. After 24 h, the solution was diluted with ether (500 mL) and washed three times with 1M HCl (200 mL), three times with saturated aqueous NaHCO₃ (200 mL), once with water (200 mL), and concentrated to give a light yellow oil (23 g). The oil was dissolved in p-dioxane (400 mL) and this solution was added to a stirring solution of LiOH.H₂O (10.3 g, 245 mmol) in water (200 mL). After stirring for 16 h, the solvents were removed by rotary evaporation and the crude residue was partitioned between ether and 1N NaOH. The ether phase was extracted twice with 1N aqueous NaOH. The combined aqueous phase was adjusted to pH 2 with 5N aqueous HCl and then extracted three times with dichloromethane. The combined dichloromethane extracts were dried with Na₂SO₄, filtered and concentrated to a white foam (17.4 g, 91%).

N-Cbz-N-Me-D-cyclohexylglycyl-proline (3)

To a suspension of potassium hydride (191.2 g (25% oil dispersion), 70 mmol) in tetrahydrofuran (75 mL) at 0° C. was added dropwise via an addition funnel a solution of N-Cbz-D-cyclohexylglycyl-proline (9 g, 23 mmol) in tetrahydrofuran (50 mL). Then a solution of methyl iodide (3 mL, 50 mmol) in tetrahydrofuran (25 mL) was added dropwise via an addition funnel [during the addition of the N-Cbz-D-cyclohexylglycyl-proline as well as the methyl iodide, the temperature was monitored internally to insure that it did not rise above 10° C.]. After 3 h, the reaction was quenched by the careful addition of glacial acetic acid (10 mL), followed by water (10 mL). The solution was poured into cold water, the pH was adjusted to 12 with 2N NaOH and the solution was extracted three times with ether. The aqueous phase was then acidified with 5N aqueous HCl and extracted three times with chloroform. The combined chloroform extracts were dried with Na₂SO₄, filtered and concentrated to give a white foam (8.4 g, 91%).

N-Me-D-cyclohexylglycyl-prolyl arginal (4)

N-Cbz-N-Me-D-cyclohexylglycyl-proline was elaborated to the tripeptide arginal by the typical three step procedure; 1) mixed anhydride coupling with Ng-Cbz-arg-lactam hydrochloride (48%) 2) lactam reduction with LiAl(Ot-Bu)₃H and 3) hydrogenolysis with H₂ and Pd/C (35% 2 step).

We claim:

1. A compound of the formula

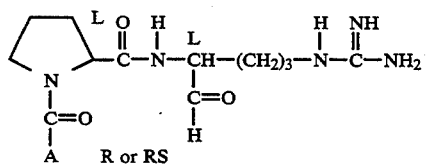

wherein A is 1) a group of the formula

wherein R is a phenyl group of the formula

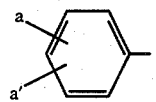

wherein a and a' independently are hydrogen, lower alkyl, lower alkoxy, halogen, trifluoromethyl, hydroxy, hydroxymethyl, amino, or aminomethyl; or R is thienyl, furyl, naphthyl, or naphthyl mono- or disubstituted by lower alkyl, lower alkoxy, halogen, amino, mono- or di-(lower alkyl) amino, or hydroxy; or R is cyclohexadienyl, cyclohexenyl, cyclohexyl or cyclopentyl;

$R_1$ is hydrogen, methyl or ethyl;

B is lower alkyl, lower alkoxy, hydroxy, or an amino group of the formula

—N($R_2$)($R_3$)

wherein $R_2$ and $R_3$ independently are hydrogen or lower alkyl or $R_2$ is hydrogen and $R_3$ is acetyl, haloacetyl or an oxycarbonyl group of the formula $R_4$—O—C(O)— wherein $R_4$ is $C_1$-$C_6$ alkyl, $C_2$-$C_6$ alkenyl, $C_3$-$C_7$ cycloalkyl, benzyl, nitrobenzyl, diphenylmethyl, or a phenyl group as defined above; provided that when $R_1$ is methyl or ethyl then B is other than methyl or ethyl or A is 2) 1-aminocyclohexyl or 1-aminocyclopentyl wherein the amino group is an —N($R_2$)($R_3$) group as defined above; or A is 3) a bicyclic group of the formula

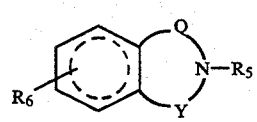

wherein Q is a one carbon radical represented by >C=O, —CH$_2$—, and

or a two carbon radical represented by —CH$_2$—CH$_2$—,

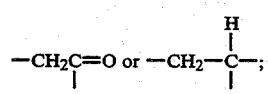

Y is a one carbon radical represented by —CH$_2$—,

or a two carbon radical represented by

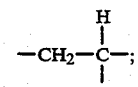

provided that one, but not both, of Q and Y is

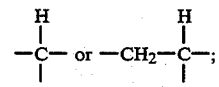

and, provided further that, only one of Q and Y is a two carbon radical;

$R_5$ is hydrogen or an oxycarbonyl group as defined above; and $R_6$ is hydrogen, halogen, hydroxy, lower alkyl or lower alkoxy; and the dotted circle within the 6-membered ring indicates that the ring is aromatic or a perhydro ring;

and the pharmaceutically acceptable non-toxic salts thereof.

2. The compound of claim 1 wherein A is a group of the formula

3. The compound of claim 2 wherein B is an amino group of the formula —N($R_2$)($R_3$).

4. The compound of claim 3 wherein $R_2$ is hydrogen or lower alkyl and $R_3$ is an oxycarbonyl group, $R_4$—O—C(O)—.

5. The compound of claim 4 wherein $R_4$ is $C_1$-$C_6$ alkyl.

6. The compound of claim 5 wherein R is a phenyl group of the formula

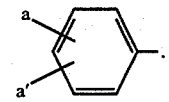

7. The compound of claim 6 said compound being N-Boc-D-phenylglycyl-L-prolyl-L-arginal and the pharmaceutically acceptable non-toxic salts thereof.

8. The compound of claim 6 said compound being N-Boc-D-(4-hydroxy)phenylglycyl-L-prolyl-L-arginal and the pharmaceutically acceptable non-toxic salts thereof.

9. The compound of claim 6 said compound being N-Boc-D-(4-methoxy)phenylglycyl-L-prolyl-L-arginal and the pharmaceutically acceptable non-toxic salts thereof.

10. The compound of claim 6 said compound being N-methyl-N-Boc-D-phenylglycyl-L-prolyl-L-arginal and the pharmaceutically acceptable non-toxic salts thereof.

11. The compound of claim 6 said compound being N-Boc-D-(3,4-dichloro)phenylglycyl-L-prolyl-L-arginal and the pharmaceutically acceptable non-toxic salts thereof.

12. The compound of claim 4 wherein R is naphthyl or substituted naphthyl.

13. The compound of claim 12 said compound being N-Boc-D-1-naphthylglycyl-L-prolyl-L-arginal and the pharmaceutically acceptable non-toxic salts thereof.

14. The compound of claim 12 said compound being N-Boc-D-2-naphthylglycyl-L-prolyl-L-arginal and the pharmaceutically acceptable non-toxic salts thereof.

15. The compound of claim 3 wherein $R_2$ and $R_3$ independently are hydrogen or lower alkyl.

16. The compound of claim 15 said compound being D-phenylglycyl-L-prolyl-L-arginal and the pharmaceutically acceptable non-toxic salts thereof.

17. The compound of claim 15 said compound being N-methyl-D-phenylglycyl-L-prolyl-L-arginal and the pharmaceutically acceptable non-toxic salts thereof.

18. The compound of claim 5 wherein R is thienyl or furyl.

19. The compound of claim 3 wherein R is cyclohexadienyl, cyclohexenyl, cyclohexyl or cyclopentyl.

20. The compound of claim 19 said compound being N-Boc-D-cyclohexylglycyl-L-prolyl-L-arginal and the pharmaceutically acceptable non-toxic salts thereof.

21. The compound of claim 19 said compound being N-methyl-D-cyclohexylglycyl-L-prolyl-L-arginal.

22. The compound of claim 2 wherein B is lower alkyl, lower alkoxy or hydroxyl and R is a phenyl group.

23. The compound of claim 1 wherein A is a bicyclic group of the formula

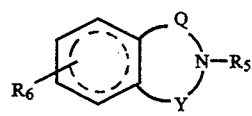

and the pharmaceutically acceptable non-toxic salts thereof.

24. The compound of claim 23 wherein A is

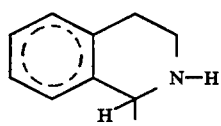

selected from the group consisting of racemic mixtures, substantially pure isomers and pharmaceutically acceptable salts thereof.

25. The compound of claim 24 which is the substantially pure D-isomer.

26. The sulfate salt of the compound of claim 25.

27. The compound of claim 23 wherein A is

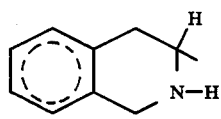

selected from the group consisting of racemic mixtures, substantially pure isomers and pharmaceutically acceptable salts thereof.

28. The substantially pure D-isomer of the compound of claim 27.

29. The sulfate salt of the compound of claim 27.

30. The compound of claim 23 wherein A is

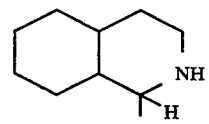

and pharmaceutically acceptable salts thereof.

31. The compound of claim 30 which is the substantially pure isomer having the structure

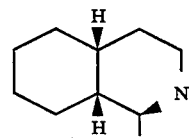

and pharmaceutically acceptable salts thereof.

32. The compound of claim 30 which is the substantially pure isomer having the structure

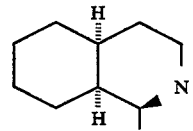

and pharmaceutically acceptable salts thereof.

33. The compound of claim 30 which is the substantially pure isomer having the structure

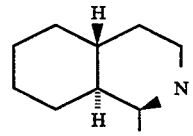

and pharmaceutically acceptable salts thereof.

34. The compound of claim 30 which is the substantially pure isomer having the structure

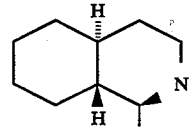

and pharmaceutically acceptable salts thereof.

35. The sulfate salt of the compound of claim 30.

36. The compound of claim 23 wherein A is

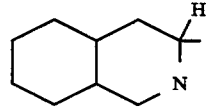

selected from the group consisting of racemic mixtures, substantially pure isomers and pharmaceutically acceptable salts thereof.

37. The compound of claim 36 which is the substantially pure isomer

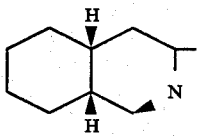

and pharmaceutically acceptable salts thereof.

38. The compound of claim 36 which is the substantially pure isomer

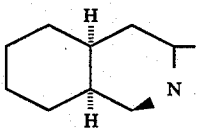

and pharmaceutically acceptable salts thereof.

39. The compound of claim 36 which is the substantially pure isomer

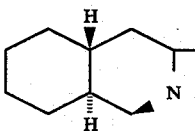

and pharmaceutically acceptable salts thereof.

40. The compound of claim 36 which is the substantially pure isomer

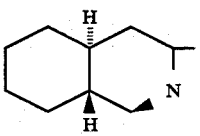

and pharmaceutically acceptable salts thereof.

41. The sulfate salt of the compound of claim 36.

42. A method for inhibiting clot formulation in mammals which comprises administering to said mammal an effective non-toxic clot inhibiting amount of a compound to claim 1.

43. The method of claim 42 wherein said compound, B is an amino group —$N(R_2)(R_3)$.

44. The method of claim 43 wherein N-Boc-D-phenylglycyl-L-prolyl-L-arginal or a pharmaceutically acceptable salt thereof is administered.

45. The method of claim 44 wherein N-methyl-D-phenylglycyl-L-prolyl-L-arginal or a pharmaceutically acceptable salt thereof is administered.

46. The method of claim 42 wherein said compound, A is a bicyclic group.

47. The method of claim 46 wherein D-1,2,3,4-tetrahydroisoquinolin-1-carbonyl-L-prolyl-L-arginine aldehyde is administered in the form of a racemic mixture, a substantially pure isomer or a pharmaceutically acceptable salt.

48. The method of claim 46 wherein D-1,2,3,4-tetrahydroisoquinolin-3-carbonyl-L-prolyl-L-arginine aldehyde is administered in the form of a racemic mixture, a substantially pure isomer or a pharmaceutically acceptable salt.

49. The method of claim 46 wherein D-perhydroisoquinolin-1-carbonyl-L-prolyl-L-arginine aldehyde is administered in the form of a racemic mixture, a substantially pure isomer or a pharmaceutically acceptable salt.

50. The method of claim 46 wherein D-perhydroisoquinolin-3-carbonyl-L-prolyl-L-arginine aldehyde is administered in the form of a racemic mixture, a substantially pure isomer or a pharmaceutically acceptable salt.

51. A pharmaceutical formulation which comprises an effective clot inhibiting amount of a compound of claim 1 and a pharmaceutically acceptable carrier.

52. A method of inhibiting thrombin in humans and animals comprising administering to a human or animal requiring thrombin inhibition an effective amount of a compound of claim 1.

53. The method of claim 52 wherein in said compound, B is an amino group —$N(R_2)(R_3)$.

54. The method of claim 53 wherein N-Boc-D-phenylglycol-L-prolyl-L-arginal or a pharmaceutically acceptable non-toxic salt thereof is administered.

55. The method of claim 53 wherein N-methyl-D-phenylglycyl-L-prolyl-L-arginal or a pharmaceutically acceptable non-toxic salt thereof is administered.

56. The method of claim 52 wherein in said compound, A is a bicyclic group.

57. The method of claim 56 wherein D-1,2,3,4-tetrahydroisoquinolin-1-carbonyl-L-prolyl-L-arginine aldehyde is administered in the form of a racemic mixture, a substantially pure isomer or a pharmaceutically acceptable salt.

58. The method of claim 56 wherein D-1,2,3,4-tetrahydroisoquinolin-3-carbonyl-L-prolyl-L-arginine aldehyde is administered in the form of a racemic mixture, a substantially pure isomer or a pharmaceutically acceptable salt.

59. The method of claim 56 wherein D-perhydroisoquinolin-1-carbonyl-L-prolyl-L-arginine aldehyde is administered in the form of a racemic mixture, a substantially pure isomer or a pharmaceutically acceptable salt.

60. The method of claim 56 wherein D-perhydroisoquinolin-3-carbonyl-L-prolyl-L-arginine aldehyde is administered in the form of a racemic mixture, a substantially pure isomer or a pharmaceutically acceptable salt.

* * * * *

UNITED STATES PATENT AND TRADEMARK OFFICE
CERTIFICATE OF CORRECTION

PATENT NO. : 5,430,023
DATED : July 4, 1995
INVENTOR(S) : Paul D. Gesellchen et al It is certified that error appears in the above-indentified patent and that said Letters Patent is hereby corrected as shown below:

Claim 22, line 2, which is Column 33, line 26, "hydroxyl" should read
-- hydroxy --.

Claim 42, line 4, Column 35, line 44, "to claim 1" should read
-- of claim 1 --.

Signed and Sealed this

Seventeenth Day of October, 1995

Attest:

BRUCE LEHMAN

*Attesting Officer*  *Commissioner of Patents and Trademarks*